United States Patent
Fofanova et al.

(10) Patent No.: US 12,337,311 B2
(45) Date of Patent: Jun. 24, 2025

(54) ENGINEERING NOVEL ENTEROID MODELS FOR UNDERSTANDING HUMAN ENTERIC DISEASE

(71) Applicants: Baylor College of Medicine, Houston, TX (US); William Marsh Rice University, Houston, TX (US)

(72) Inventors: Tatiana Y. Fofanova, Houston, TX (US); Jennifer Auchtung, Houston, TX (US); Reid Laurence Wilson, Houston, TX (US); Christopher Stewart, Houston, TX (US); Joseph Petrosino, Houston, TX (US); Robert Allen Britton, Houston, TX (US); Jane Grande-Allen, Houston, TX (US); Noah F. Shroyer, Houston, TX (US); Mary K. Estes, Houston, TX (US)

(73) Assignees: Baylor College of Medicine, Houston, TX (US); William Marsh Rice University, Houston, TX (US)

( * ) Notice: Subject to any disclaimer, the term of this patent is extended or adjusted under 35 U.S.C. 154(b) by 1055 days.

(21) Appl. No.: 16/757,577

(22) PCT Filed: Oct. 26, 2018

(86) PCT No.: PCT/US2018/057832
§ 371 (c)(1),
(2) Date: Apr. 20, 2020

(87) PCT Pub. No.: WO2019/084484
PCT Pub. Date: May 2, 2019

(65) Prior Publication Data
US 2020/0269230 A1 Aug. 27, 2020

Related U.S. Application Data

(60) Provisional application No. 62/577,221, filed on Oct. 26, 2017.

(51) Int. Cl.
*B01L 1/02* (2006.01)
*B01L 3/00* (2006.01)
(Continued)

(52) U.S. Cl.
CPC ............ *B01L 1/025* (2013.01); *B01L 3/5085* (2013.01); *C12M 25/02* (2013.01); *C12M 25/04* (2013.01);
(Continued)

(58) Field of Classification Search
CPC .. B01L 1/025; B01L 3/5085; B01L 2300/042; B01L 2300/048; C12M 25/02;
(Continued)

(56) References Cited

U.S. PATENT DOCUMENTS

| | | | |
|---|---|---|---|
| 4,111,753 A * | 9/1978 | Folsom | ................. C12M 41/14 435/801 |
| 5,116,506 A | 5/1992 | Williamson et al. | |

(Continued)

FOREIGN PATENT DOCUMENTS

| JP | 2014113511 A | 6/2014 |
|---|---|---|
| WO | 2006/037022 A2 | 4/2006 |

OTHER PUBLICATIONS

Eain et al., (Feb. 2017), Engineering solutions for representative models of the gastrointestinal human-microbe interface. Engineering, 3(1), 60-65. (Year: 2017).*

*Primary Examiner* — Michael L Hobbs
(74) *Attorney, Agent, or Firm* — Norton Rose Fulbright US LLP

(57) ABSTRACT

An anaerobic chamber system to evaluate human enteric disease is described herein that can be used to test therapeutic components. In specific embodiments, the anaerobic chamber is used to determine the effect of one or more bacterial communities on ex vivo enteroid cultures. In one (Continued)

application, the anaerobic chamber system is used to determine the efficacy of therapeutic components in ameliorating human enteric disease using personalized medicine.

27 Claims, 26 Drawing Sheets

(51) Int. Cl.
  *C12M 1/12* (2006.01)
  *C12M 1/34* (2006.01)
  *C12N 1/14* (2006.01)
  *C12N 7/00* (2006.01)
  *C40B 30/06* (2006.01)
  *G01N 33/50* (2006.01)
  *G01N 33/569* (2006.01)

(52) U.S. Cl.
  CPC .............. *C12M 41/34* (2013.01); *C12N 1/14* (2013.01); *C12N 7/00* (2013.01); *C40B 30/06* (2013.01); *G01N 33/5008* (2013.01); *G01N 33/569* (2013.01); *B01L 2300/042* (2013.01); *B01L 2300/048* (2013.01)

(58) Field of Classification Search
  CPC ...... C12M 25/04; C12M 41/34; C12M 23/12; C12N 7/00; C12N 1/14; C40B 30/06; G01N 33/5008; G01N 33/569; G01N 33/4833; G01N 2500/10; G01N 2800/52; G01N 2033/4977
  See application file for complete search history.

(56) References Cited

U.S. PATENT DOCUMENTS

| | | | | |
|---|---|---|---|---|
| 5,459,069 | A * | 10/1995 | Palsson | C07K 14/535 |
| | | | | 435/293.1 |
| 5,470,743 | A * | 11/1995 | Mussi | C12M 29/04 |
| | | | | 435/297.5 |
| 8,501,462 | B2 * | 8/2013 | Eddington | C12M 25/04 |
| | | | | 435/297.2 |
| 10,876,089 | B2 * | 12/2020 | Zhang | B29C 39/026 |
| 2009/0142627 | A1 | 6/2009 | Shimomura et al. | |
| 2017/0088807 | A1 | 3/2017 | Kim | |
| 2018/0282704 | A1 * | 10/2018 | Estes | C12N 7/02 |
| 2018/0346867 | A1 * | 12/2018 | Oliver | C12M 23/16 |

* cited by examiner

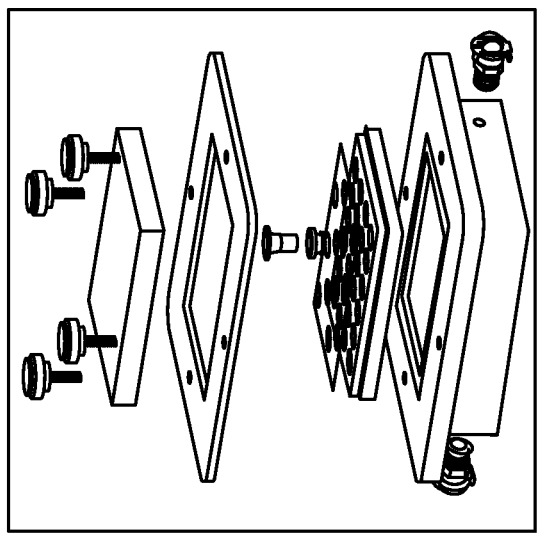
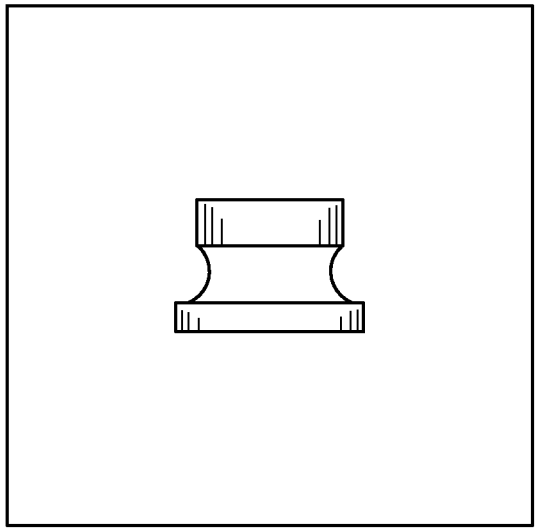
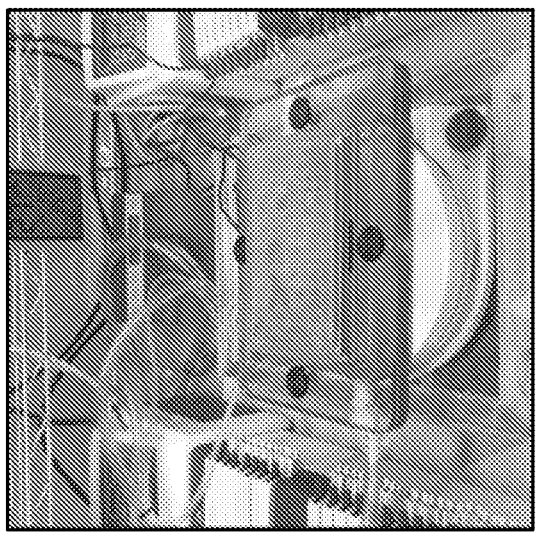
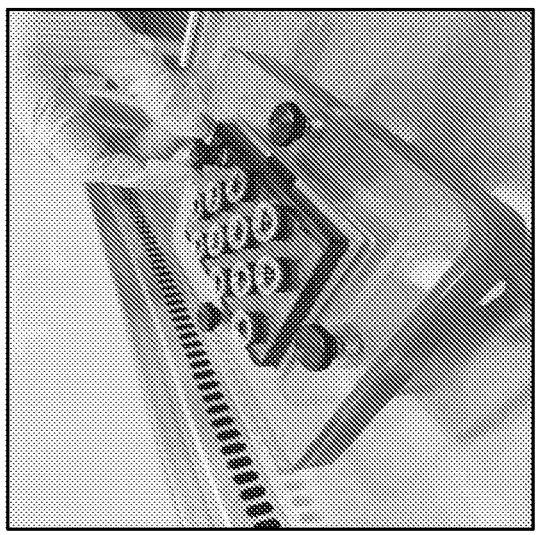
FIG. 1D

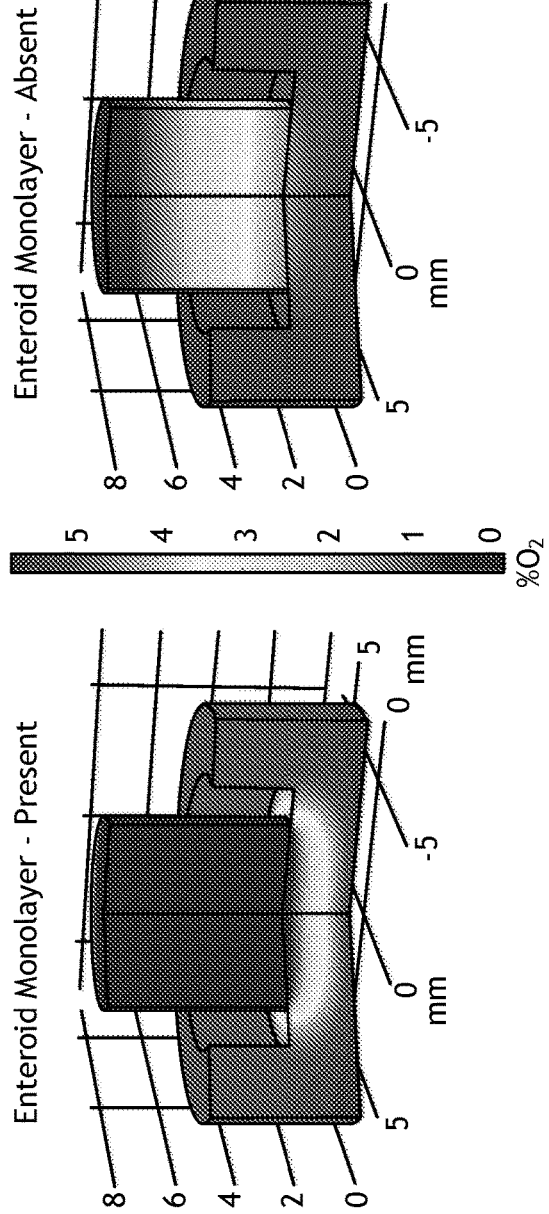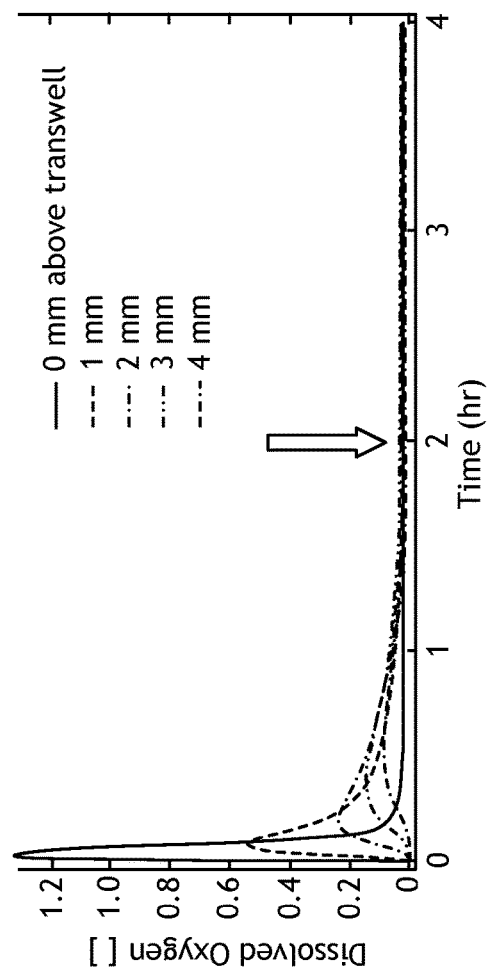
FIG. 2A
FIG. 2B

Steep Oxygen Gradient:
Following delivery of 5.6% and 10.2% $O_2$ blood gas, the basolateral side is oxygenated while the apical side is effectively anaerobic.
Healthy Enteroids:
Enteroids monolayers imaged after 24hrs at 5% basolateral oxygen are polarized (Villin stain in red), show an intact mucus layer (Alcian blue stain) and normal morphology
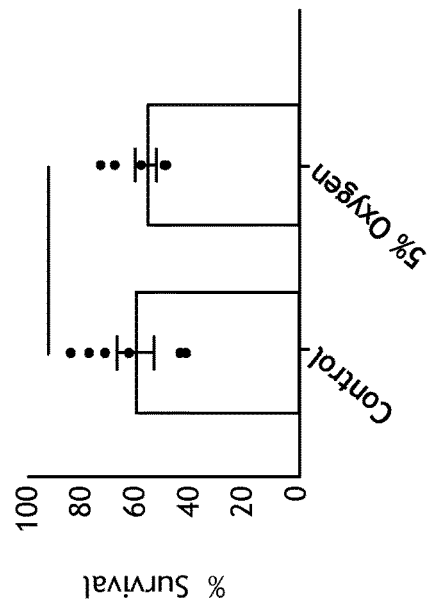
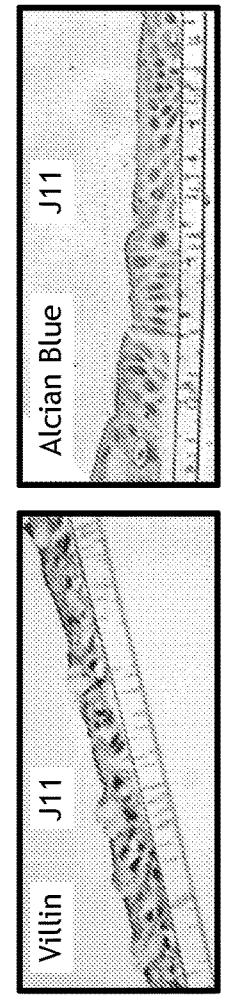
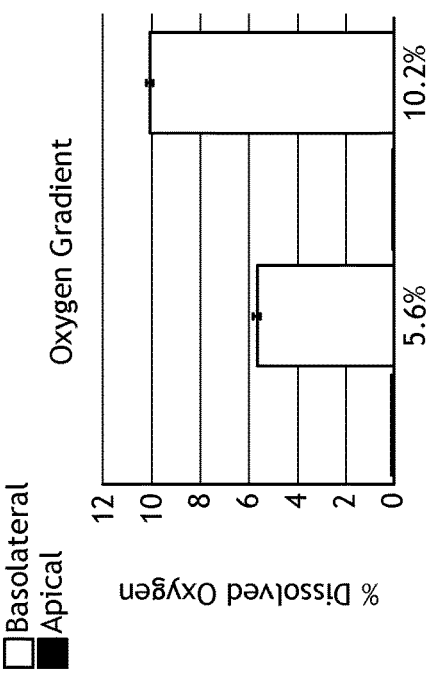
FIG. 4

- Survey of 106 tight junction and innate anti-microbial response genes
- Broad-scale upregulation across multiple patient-derived enteroid lineages

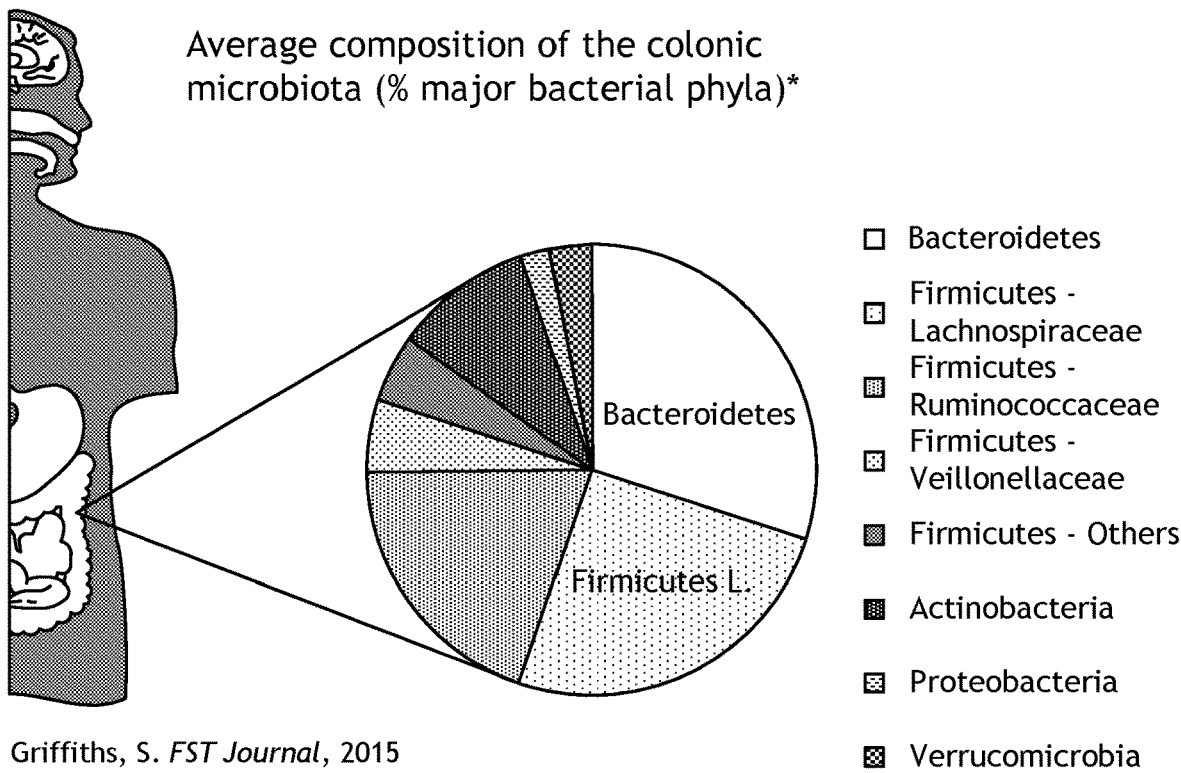

Average composition of the colonic microbiota (% major bacterial phyla)*

- ☐ Bacteroidetes
- Firmicutes - Lachnospiraceae
- Firmicutes - Ruminococcaceae
- Firmicutes - Veillonellaceae
- Firmicutes - Others
- Actinobacteria
- Proteobacteria
- Verrucomicrobia Griffiths, S. *FST Journal*, 2015

Bacteroides thetaiotamicron
- Bacteroidetes
- Gram-negative nanoanaerobe
- Common, abundant commensal
- Acetate production Clinical implications:
Associated with remission in UC/Crohns

*Blautia sp. 30188*
- Firmicutes
- Gram-positive obligate anaerobe
- Common, abundant commensal
- Lactate and Acetate production Clinical implications:
Reduced incidence of GvH disease

FIG. 8

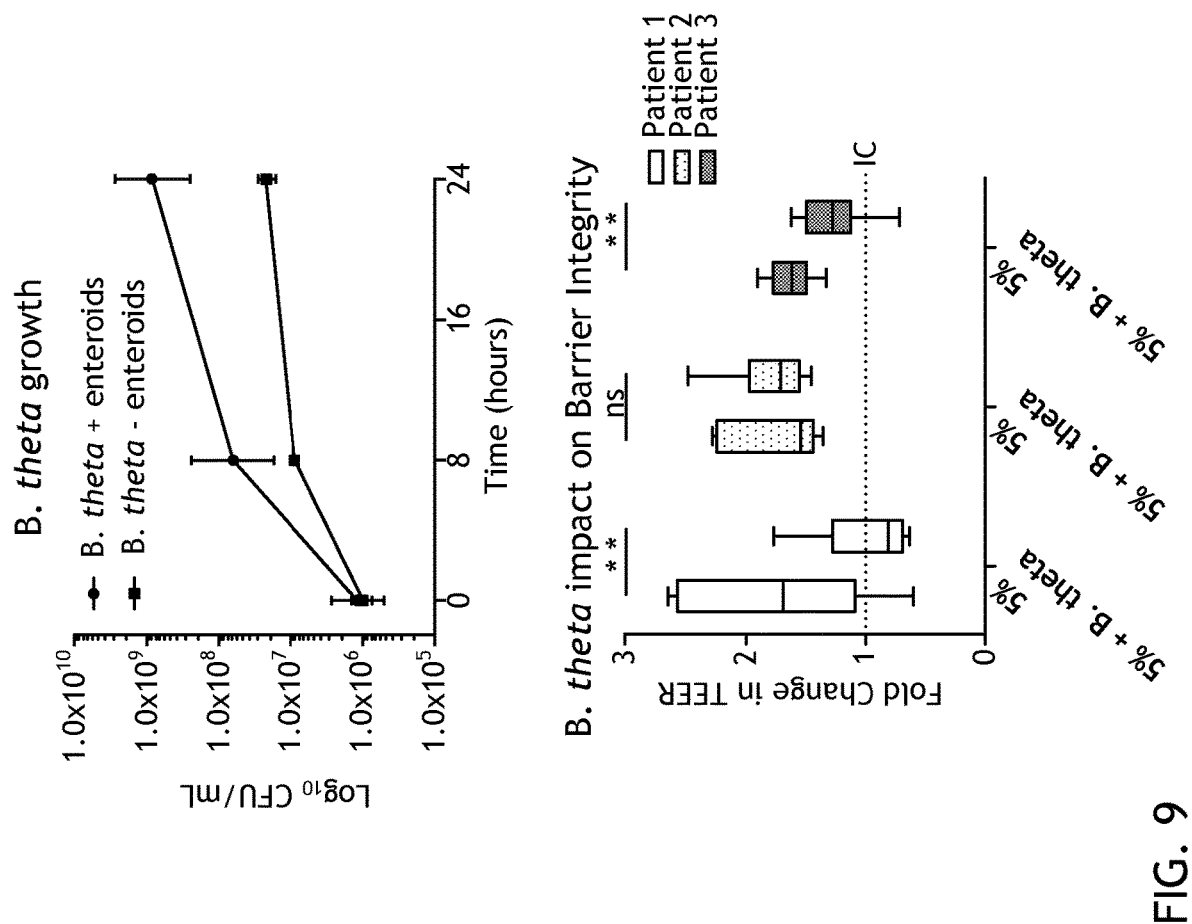
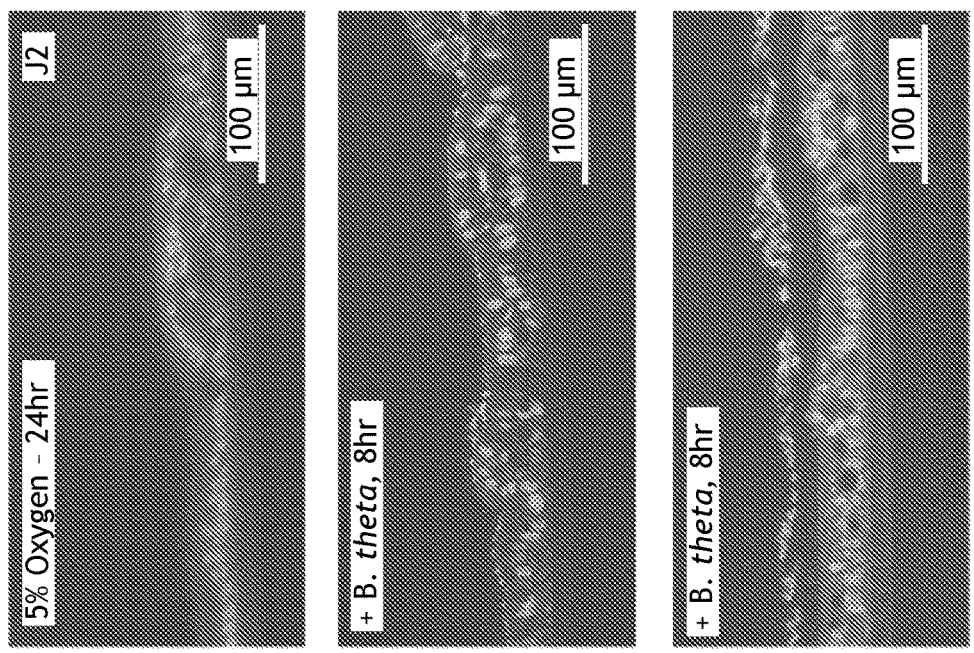
FIG. 9

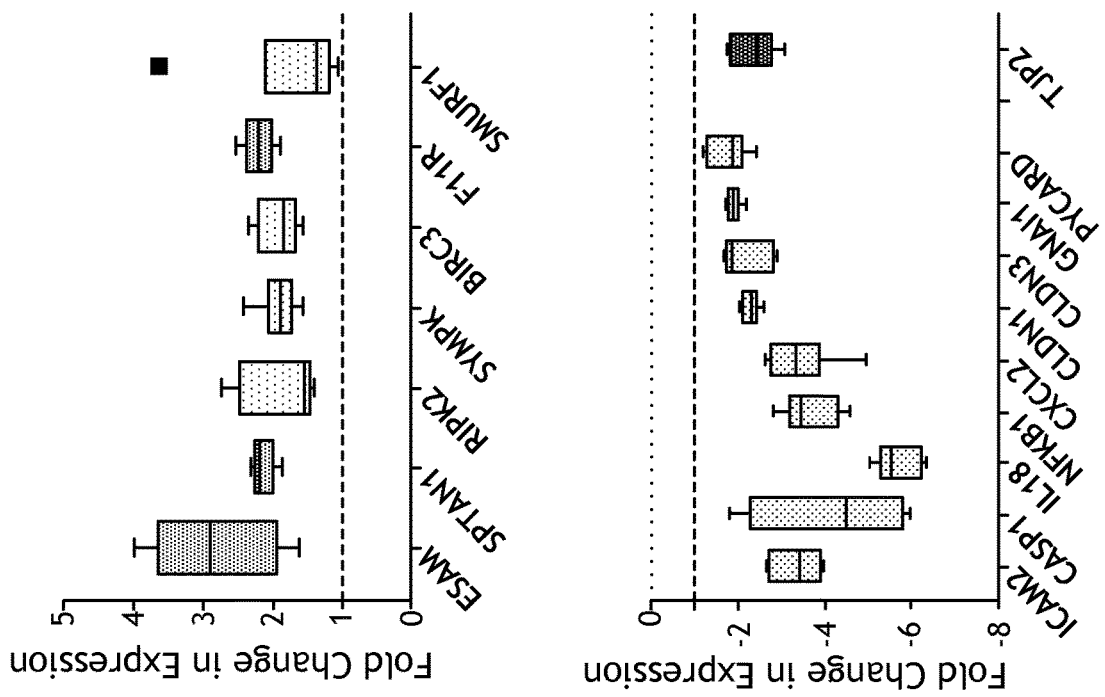
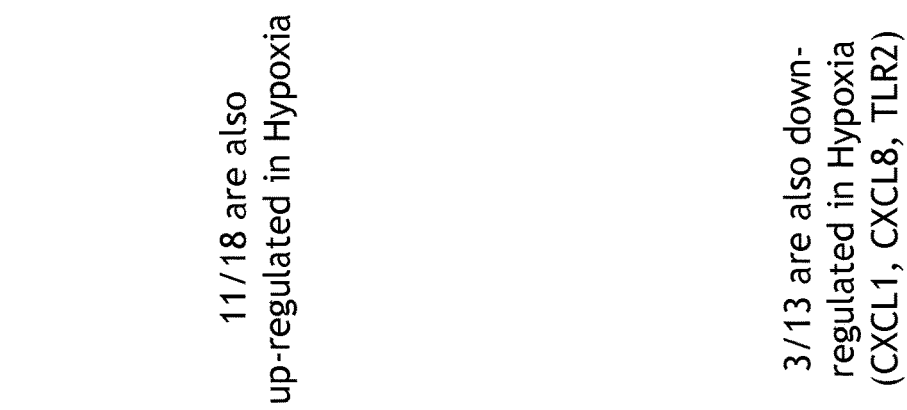
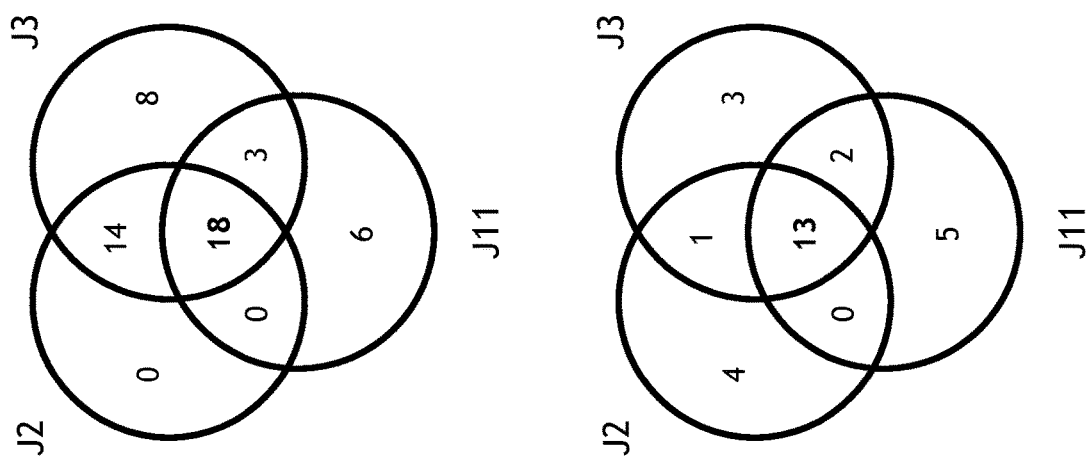
FIG. 13

| GO-ID | Description | Corrected P-Value | Cluster Frequency | Genes |
|---|---|---|---|---|
| 45429 | Positive regulation of nitric oxide biosynthesis process | 1.9214E-8 | 6/33 (18.1%) | HSP90AA1 IL1B AKT1 TICAM1 TLR4 TLR2 |
| 43123 | Positive regulation of I-kB kinase/NF-kB cascade | 5.1691E-8 | 8/33 (24.2%) | VAPA IL1B TLR6 TICAM1 TLR4 RELA RHOA MYD88 |
| 2221 | Pattern recognition receptor signaling pathway | 6.9208E-8 | 5/33 (15.1%) | TLR6 TICAM TLR4 RELA TLR2 |
| 326755 | Regulation of IL-6 production | 6.9208E-8 | 6/33 (18.1%) | IL1B TLR6 TICAM TLR4 MYD88 TLR2 |
| 10647 | Positive regulation of cell communication | 1.1126E-7 | 11/33 (33.3%) | VAPA IL1B RAC1 TLR6 TICAM1 HIF1A TLR4 RHOA RELA MYD88 TLR2 |
| 6954 | Inflammatory Response | 1.1785E-7 | 10/33 (30.3%) | CXCL8 IL1B AKT1 CXCL1 RAC1 TLR6 TICAM1 HIF1A TLR4 RELA |
| 7163 | Establishment of maintenance of cell polarity | 3.195E-6 | 5/33 (15.1%) | CDC42 PRKCI PARD3 LLGL1 MARK2 |

FIG. 15B

| GO-ID | Description | Corrected P-Value | Cluster Frequency | Genes |
|---|---|---|---|---|
| 42127 | Regulation of Cell Proliferation | 9.79E-03 | 7/31 22.5% | MAP2K1 CXCL8 RIPK2 IL18 CXCL1 TLR4 RELA |
| 6954 | Inflammatory Response | 3.26E-05 | 8/31 25.8% | CXCL8 RIPK2 CXCL1 F11R CXCL2 TLR4 RELA NFKB1 |
| 44419 | Interspecies Interaction Between Organisms | 7.92E-04 | 6/31 19.3% | IRF7 F11R CLDN1 TLR4 RELA TLR2 |
| 2758 | Innate Immune Response Activating Signal Transduction | 1.86E-05 | 4/31 12.9% | RIPK2 TLR4 RELA TLR2 |
| 1819 | Positive Regulation of Cytokine Production | 1.86E-05 | 6/31 19.3% | PYCARD RIPK2 CASP1 IL18 TLR4 TLR2 |
| 51092 | Positive Regulation of Nf-kb TF Activity | 1.86E-05 | 5/31 16.1% | PYCARD RIPK2 TLR4 RELA TLR2 |
| 2237 | Response to Molecule of Bacterial Origin | 2.41E-04 | 5/31 16.1% | RIPK2 CASP1 TLR4 RELA TLR2 |

FIG. 17

ENGINEERING NOVEL ENTEROID MODELS FOR UNDERSTANDING HUMAN ENTERIC DISEASE

CROSS-REFERENCE TO RELATED APPLICATIONS

This application is a national phase application under 35 U.S.C. § 371 that claims priority to International Application No. PCT/US2018/057832 filed Oct. 26, 2018, which claims priority to U.S. Provisional Patent Application Ser. No. 62/577,221, filed Oct. 26, 2017, both of which are incorporated by reference herein in their entirety.

STATEMENT REGARDING FEDERALLY SPONSORED RESEARCH OR DEVELOPMENT

This invention was made with government support under 1 U19 AI116497-01 awarded by NIH/NIAID. The government has certain rights in the invention.

TECHNICAL FIELD

Embodiments of the disclosure encompass at least the fields of cell biology, molecular biology, physiology, microbiology, and medicine.

BACKGROUND

Mechanistic investigations of host-microbe interactions in the human gut are severely limited because of two principal challenges. The first is morphological because the intestinal epithelium is oxygen-dependent while most gut bacteria are obligate anaerobes; this creates an exceptionally steep oxygen gradient across the single-cell-thick epithelial layer, making it difficult to recreate a physiologically relevant intestinal epithelial monolayer. The second challenge is that the intestinal epithelium is in a state of chronic low-grade inflammation. The gut is a large, immunogenic organ and constant exposure to luminal antigens, sampled by immune cells, are responsible for tolerance in the gut. Immune cells enter the epithelium and consume the residual oxygen. As a result, the gut is in a chronic state of reduced oxygen referred to as physioxia/hypoxia that is its normal state. During inflammatory bowel disease, for example, more immune cells infiltrate the gut and the level of available oxygen reduces even further. However, a standard cell culture incubator does not replicate the physiologically normal state of hypoxia and, in fact, in some cases it is comparatively hyperoxic. This is relevant because a hypoxic epithelium interacts with bacteria in a fundamentally different way: it boosts barrier integrity, produces anti-microbial peptides, etc. By failing to perform studies under physiologically relevant oxygen concentrations, one could produce unreliable results.

The present disclosure provides a solution to a long-felt need in the art of culture of gut tissue in the form of enteroids in a physiologically relevant environment.

BRIEF SUMMARY

The present disclosure is directed to systems, methods, and compositions that allow physiologically relevant co-culture of anaerobic microbes with gut tissues, including those gut tissues configured as enteroids. Enteroids provide a useful opportunity for studying disease at the epithelial level, including diseases such as irritable bowel syndrome, Crohn's disease, microbe infection, Ulcerative Colitis, Celiac disease, diverticulitis, and so forth.

To address deficiencies in the art, the inventors developed a simple, cost-effective method for co-culturing microbes with gut tissues under variable oxygen conditions. In specific embodiments, obligate anaerobic bacteria were co-cultured with human intestinal enteroid monolayers under variable oxygen conditions. Microbes in the mammalian gastrointestinal system are known to influence metabolism and therapeutic success. Cultivated enteroids retain the genetic background and susceptibility of the host from which the enteroid was obtained. Such replication of the host's pre-existing phenotype in the cultivated enteroid provides the opportunity to characterize host-microbe interactions. Furthermore, the co-culturing system also provides the opportunity to advance patient care by means of personalized medicine.

Embodiments of the disclosure include the development and optimization of a novel co-culture system to evaluate the efficacy of one or more therapies ex vivo. Thus, in specific embodiments the system allows drug discovery in an environment that closely mimics the gut in vivo. In specific embodiments, the therapy itself may comprise one or more drugs or one or more bacteria, including probiotic bacteria, for example. In additional embodiments, the therapy being tested is exposed to gut tissues prior to, during, and/or after exposure of the gut tissues to one or more bacteria.

Embodiments of the disclosure encompass the assembly and use of an Enteroid-Anaerobe Co-Culture (EACC) system that provides for physiologically relevant oxygen control for cultivated enteroid(s) to recapitulate the phenotype and response of a host.

Embodiments of the disclosure include systems comprising an anaerobic chamber, an aerobic chamber, and a gas adjustable chamber. In some cases, there is a first gas permeable side common to the anaerobic and the aerobic chamber and a second gas permeable side common to the aerobic and the gas adjustable chamber. Part or the entire system maybe housed in an anaerobic atmosphere. In specific cases, the gas adjustable chamber comprises a mechanism for circulation. The gas adjustable chamber may be configured to receive gas via a conduit. A source of the gas may be a tank, and the gas may be blood gas, such as gas comprised of oxygen, carbon dioxide, and nitrogen. In specific embodiments, the anaerobic chamber is extractable, and it may be adapted to be mounted on one or more gaskets. The aerobic chamber may comprise one or more multi-well plates. At least part of the aerobic chamber may comprise glass. In some cases, the second gas permeable side comprises one or more openings. In particular embodiments, a two-sided adhesive is mounted onto the first gas permeable side in the anaerobic chamber. The anaerobic chamber may be adapted to be mounted onto the aerobic chamber, and an adapter may be mounted onto the aerobic chamber. The adapter may be secured onto the aerobic chamber and the gas adjustable chamber. In some cases, the system comprises a lid.

In particular embodiments, the system comprises one or more cultured gut tissues of a subject in the anaerobic chamber, and the gut tissue may comprise one or more enteroids. The gut tissue may be plated as a monolayer and differentiated within the anaerobic chamber. The anaerobic chamber may comprise one or more microbes, such as bacteria viruses, and or fungi. In some cases, the anaerobic chamber comprises media for the enteroid cultures, and in specific cases, the media for the enteroid cultures comprises one or more growth factors in the anaerobic chamber.

In embodiments of the disclosure, there are methods of determining the efficacy of one or more therapies for one or more medical conditions comprising the step of exposing the one or more therapies to any system encompassed herein. In specific embodiments, the anaerobic chamber is exposed to blood gas through the first gas permeable side and the aerobic chamber is exposed to blood gas through the second gas permeable side via the gas adjustable chamber. The enteroid cultures may be produced from gut tissue from a human or a non-human mammal. The enteroid cultures may be plated in a monolayer as differentiated cells on the anaerobic chamber. In specific embodiments, one or more microbes are provided to the enteroid cultures prior to, during, and/or after the exposure of the system to one or more therapies. The one or more microbes may be obtained from fecal matter. In specific embodiments the efficacy of the one or more therapies to one or more gut tissues of a subject are monitored by assaying the cell barrier integrity, assaying the gene expression of one or more genes, assaying the protein levels and/or identity of one or more proteins and/or assaying the histology of the enteroid culture. Cell barrier integrity may be assayed by trans epithelial electrical resistance. The gene expression levels and/or their identity may be assayed by quantitative reverse transcription polymerase chain reaction, hybridization, and/or sequencing. The protein(s) levels and/or their identity may be assayed by electron microscopy, ELISA, western blot, mass spectrometry, or a combination thereof. The protein(s) levels and/or their identity may assayed by an antibody, including one or more that may or may not be labeled.

In some embodiments, there are methods of determining a suitable therapy of a subject with a medical condition comprising the step of exposing one or more therapies to any system encompassed herein, wherein the gut tissue is from the subject.

In certain embodiments, there are methods of producing any system encompassed herein, comprising the steps of providing the gut tissue to a system comprising an anaerobic chamber, an aerobic chamber, and a gas adjustable chamber. The method may further comprise the step of producing the enteroids. The method may further comprise the step of providing one or more microbes to the system. The method may further comprise the step of providing one or more therapies to the system.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding of the present disclosure, reference is now made to the following descriptions taken in conjunction with the accompanying drawings..

FIG. 1 shows assembly and validation of the enteroid-anaerobe co-culture (EACC) system. FIG. 1D shows assembly of an embodiment of the enteroid-anaerobe co-culture system.

FIG. 2 shows predictive modeling of enteroid oxygen consumption that establishes examples of operational limits of the co-culture system.

FIG. 4 demonstrates that the system recapitulates in-vivo conditions.

FIG. 8 shows selection of anaerobic bacteria for the system validation.

FIG. 9 demonstrates that the EACC system supports enteroid-nanoanaerobe co-culture for at least 24 hours for *B. theta*, as an example.

FIG. 13 demonstrates specific gene expression changes following *B. theta* co culture.

FIG. 17 demonstrates gene ontology analysis for gene expression changes in response to 24 hour *B. theta* co-culture at 5% basolateral oxygen.

DETAILED DESCRIPTION

Figure 1C:
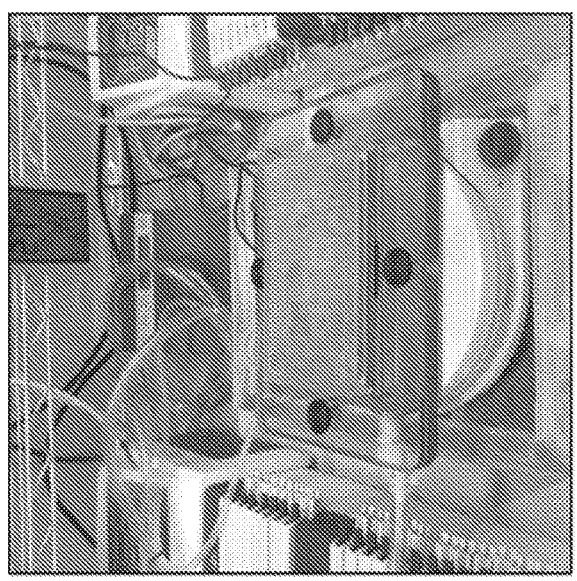
FIG. 1C shows a photograph of an example of a system in use.

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the invention may "consist essentially of" or "consist of" one or more sequences of the invention, for example. Some embodiments of the invention may consist of or consist essentially of one or more elements, method steps, and/or methods of the invention. It is contemplated that any method or composition described herein can be implemented with respect to any other method or composition described herein. The scope of the present application is not intended to be limited to the particular embodiments of the process, machine, manufacture, composition of matter, means, methods and steps described in the specification.

I. Definitions

The term "enteroid" as used herein refers to a three-dimensional culture system propagated from stem cells from intestinal crypts isolated from human surgical specimens, endoscopic biopsies, autopsy specimens, or a combination thereof.

The term "microbe" as used herein refers to a microscopic organism or particle that may exist as a particle, an acellular form, single celled form and/or in a colony of cells. The microbes can be further divided into categories; such as, bacteria, archea, fungi, protozoa, algae, and viruses. The human tract (GI) harbors a vast population of microbes that influence immune and metabolic homeostasis, as well as protection against disease. Alteration of the GI tract's microbe population is known to be associated with the pathogenesis of many inflammatory diseases and infections. In this application, the use of microbes in the anaerobic co-culture system along with gut tissue represents the normal physiological components of the GI tract. A microbe may also be evaluated for its therapeutic benefit in providing relief for enteric disease. In that instance, the therapeutic microbe will be referred to as a therapy.

II. General Embodiments

Physiological hypoxia is an important consideration when modeling host-microbe interactions among ex vivo cultures. Hypoxic tissues behave differently from normoxic tissue, including in a state of inflammation in the gut when infection needs to be curtailed. Epithelial cells under hypoxia exhibit enhanced expression of barrier protective genes and mucins to limit bacterial translocation. They selectively remodel cell membranes to hinder bacterial attachment and activate NFkB to recruit more inflammatory cells, in addition to activating other pathways to attract immune cells in greater numbers. Being able to model host-anaerobe interactions under variable conditions is useful to understanding these interactions in disease pathogenesis or studying commensals in normal gut function.

A challenge in the art is that the intestinal epithelium is oxygen-dependent while gut bacteria comprise obligate anaerobes that are killed by very low concentrations of oxygen. Embodiments of the disclosure allow ex vivo enteric model systems to be more physiologically relevant to reduce the rate of experimental error, improve reproducibility, and more accurately inform downstream in vivo (including clinical) studies. The systems of the present disclosure allow for reproduction of mammalian gut tissue in a physiologically relevant environment by providing both of (1) gut tissue in its physiological enteric environment requiring sufficient oxygen to sustain living cells; and (2) one or more enteric microbes in its physiological enteric environment requiring very little or no oxygen. The present disclosures allows one to define mechanisms of pathogenesis that cause human disease; investigate human host genetic susceptibility to enteropathogens; and understand how commensals alter pathogen-host interactions.

In particular embodiments, the systems of the disclosure facilitate host-anaerobe interaction. The disclosure provides a new way to pre-clinically validate microbial therapeutic efficacy, given that the system permits high-throughput scientific investigation and therapy evaluation, including bacteriotherapy evaluation.

Embodiments of the disclosure concern methods, systems, and/or compositions for culturing any microbe that may be found in the GI tract of any mammal, including a human, horse, pig, bovine, primate, dog, or cat, for example.

Embodiments of the disclosure relate to host-microbe interactions between human jejunal enteroids, as examples, and commensal anaerobes that differ under physiological hypoxia in a novel co-culture model system.

In some embodiments, there is a substantial difference in cell barrier integrity and gene expression profile following co-culture of the enteroids with anaerobic bacteria, demonstrating in at least some embodiments the need for a personalized medicine approach to understand host-microbe interactions.

III. Embodiments of the Anaerobic Enteric Cultivation Systems

The present disclosure provides embodiments of an anaerobic enteroid cultivation system useful for cultivation of microbes that are present in the tissues of the stomach, intestine, and/or colon. In certain embodiments, the methods and compositions concern cultivation of gastrointestinal bacteria, viruses, and/or fungi, for example. In particular embodiments, the bacteria, viruses, and/or fungi may directly or indirectly cause enteric disease. In other embodiments, the systems are useful for determining the efficacy of one or more therapies to treat enteric disease. The systems are useful for evaluating enteroid cultures of any mammal.

A. The Enteroid Anaerobe Co-Culturing System (EACC) Components

Embodiments of the EACC system of the present disclosure comprises at least an anaerobic chamber, an aerobic chamber, and a gas adjustable chamber. The separate chambers are configured in the system to provide an appropriate amount of blood gas (for example oxygen, nitrogen, and/or carbon dioxide) to enteroids in the system to sustain their healthy growth while at the same time are configured to provide an appropriate amount of anerobic gas to one or more microbes in the system (for example, anaerobic microbes). The term "anaerobic chamber" as used herein may refer to a permeable support device that can be used to perform various studies and to test therapeutic compounds, also referred to as Transwells®, in some embodiments.

In particular embodiments, an appropriate range of level of blood gas for sustaining the enteroids is not utilized for sustaining one or more microbes in the system. In particular embodiments, the range of level of permissible oxygen level for the anaerobes is lower than the range of level of oxygen for the enteroids. In specific embodiments, the blood gas comprises oxygen, carbon dioxide, and nitrogen. In a specific embodiment, a sufficient range of level of oxygen for the enteroids in the anaerobic chamber is 2-10%, depending on the physiological phenomenon being investigated and a sufficient range of level of oxygen for the microbes in the anaerobic chamber is less than 0.1%. In each of the anaerobic chamber, aerobic chamber, and gas adjustable chamber, the level of blood gas may be adjustable, including at any time. In at least some cases, a suitable level of oxygen may need to be determined empirically. The anaerobic chamber itself may be supplied with a standard anaerobic mixture (about 5% hydrogen and 95% nitrogen), in some embodiments.

In specific embodiments, the composition of the blood gas comprises the following: $CO_2$ 5%/$O_2$ 5.6%/BAL $N_2$. This formulation may be utilized as being physiologically relevant for a healthy gut. The user, however, may choose to use a lower or higher concentration of $O_2$ (for example) to mimic a disease state.

In particular embodiments, the anaerobic chamber receives an appropriate level of blood gas from the aerobic chamber via a commonly shared gas permeable side between the anaerobic chamber and aerobic chamber. In particular embodiments, the aerobic chamber receives an appropriate level of blood gas from the gas adjustable chamber via a commonly shared gas permeable side between the aerobic chamber and the gas adjustable chamber. According to the disclosure, a multi-well plate may comprise multiple aerobic chambers each having gas permeable bases. One or more gaskets may be mounted into the aerobic chamber, and aerobic chamber(s) not in use may be sealed by any suitable means, such as with a two-sided adhesive. One alternative to the adhesive may be PCR film, in some cases. Following placement of a gasket into the aerobic chamber, the extractable anaerobic chamber is mounted into the aerobic chamber. The mounted anaerobic chamber within the aerobic chamber multi-well plate is mounted onto the gas adjustable chamber.

The EACC system may comprise a multi-level chamber system, in some embodiments, wherein an anaerobic chamber is mounted into an aerobic chamber and an aerobic chamber is mounted into a gas adjustable chamber. Therein, the system's chambers must be positioned in a predetermined, closely restricted position for handling thereof.

According to a further aspect of the disclosure, the gas adjustable chamber receives oxygen through an external source, such as a blood gas tank. The blood gas may be delivered via a conduit of any type, including a tube, for example. In specific embodiments, at least one mechanism to enhance circulation of the blood gas in the gas adjustable chamber is utilized. For example, a magnetic stir bar may be placed within the gas adjustable chamber to provide mechanical movement of the blood gas into gas permeable chambers above. According to an embodiment of the disclosure, the assembled multi-level EACC system is configured to be mounted onto a stir plate. By means of rotation of the magnetic stir bar placed within the gas adjustable chamber, the blood gas is capable of being circulated to vertically mounted chambers. Such circulation allows the blood gas to reach greater vertical heights away from the source of the gas than if the mechanism to enhance circulation was not utilized.

The components of the system may be comprised of any suitable material or materials, including plastic or glass for example. The components of the system may be sterile prior to use and may be of material that can be autoclavable. The components of the system may be obtained commercially or generated by the user. The components of the system may or may not be housed together for storage or for commercial sale.

In specific embodiments, the system lacks microfluidic channels.

Figure 18:
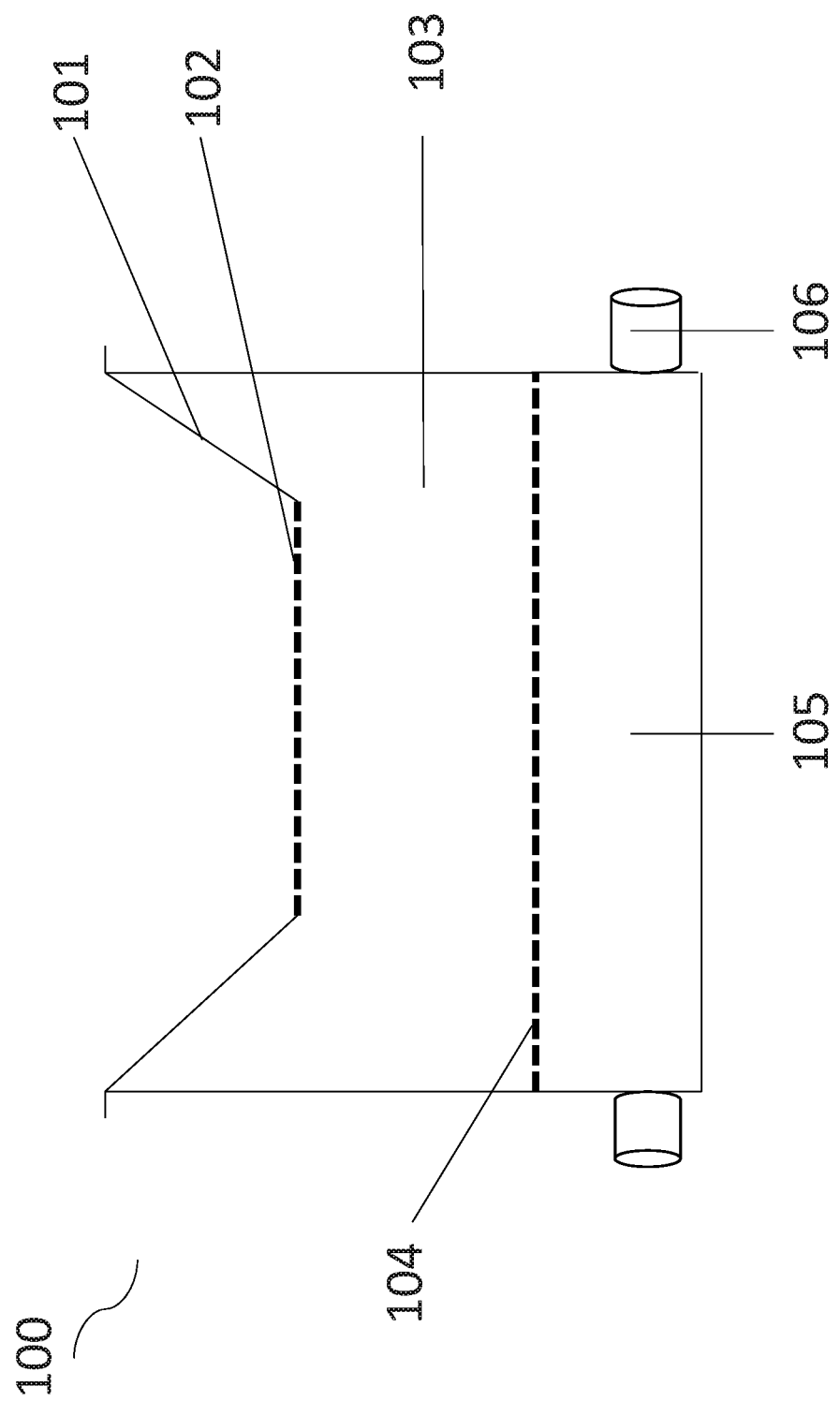
FIG. 18 illustrates one embodiment of an enteric anaerobic co-culture system.

Turning now to FIG. 18, an embodiment of an anaerobic co-culturing system 100 is provided. Within one embodiment of the anaerobic co culturing system 100, there is an anaerobic chamber 101 that comprises a gas permeable base 102 that is gaseously communicable with aerobic chamber 103. In specific embodiments, gas permeable base 102 of the anaerobic chamber is commonly shared with aerobic chamber 103. The aerobic chamber 103 also comprises gas permeable base 104 that is gaseously communicable with gas adjustable chamber 105. In specific embodiments, gas permeable base 102 of the anaerobic chamber and gas permeable base 104 of the aerobic chamber are substantially parallel to one another in the system. In specific embodiments, the system comprises one or more inlet for receiving blood gas. In particular embodiments, the system 100 comprises an outlet in the aerobic chamber to permit flow-through of blood gas, such that one can replace oxygen as it is consumed being consumed by the culture. The system 100 may or may not be housed in an anaerobic environment, such as an anaerobic hood, chamber, or room, for example.

Figure 19:
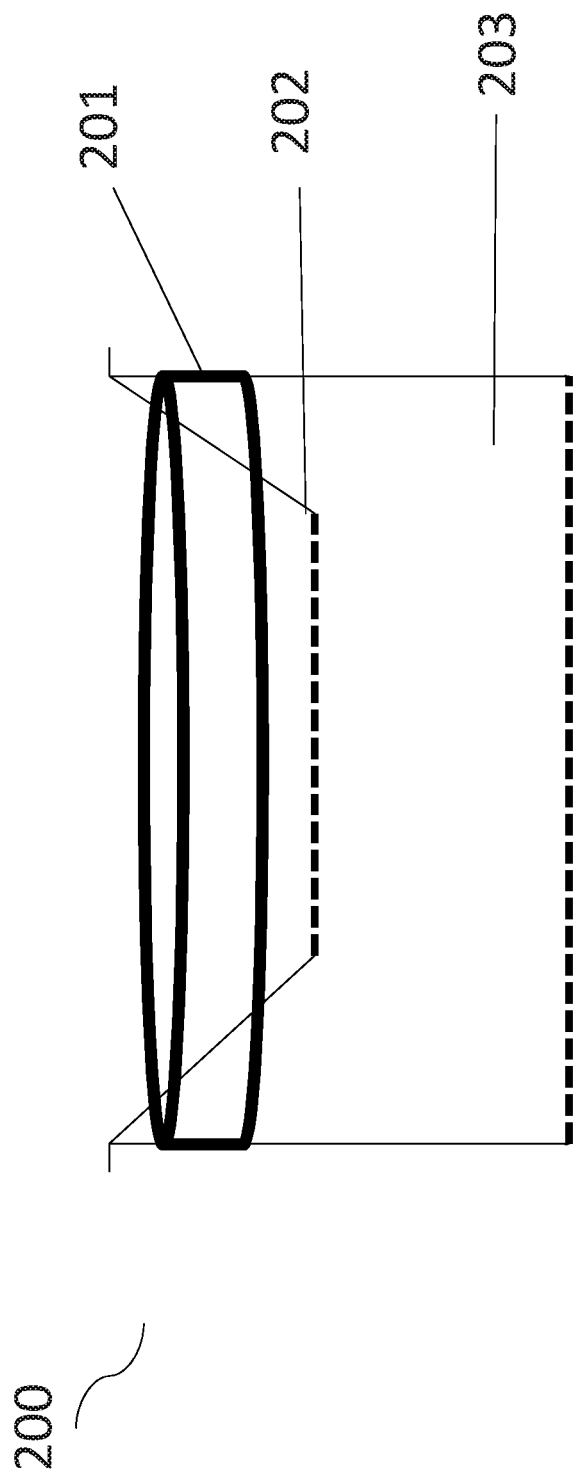
FIG. 19 illustrates one embodiment of an anaerobic chamber fitted with a gasket and mounted within an aerobic chamber.

FIG. 19 shows an additional embodiment of an anaerobic co-culturing system 200. The additional embodiment of an anaerobic co-culturing system 200 comprises a gasket 201 externally fitted to the gas permeable anaerobic chamber 202 and mounted into the gas permeable aerobic chamber 203. In specific embodiments the, gasket 201 secures the anaerobic chamber 202 within the aerobic chamber 203. The gasket support 201 sits within the aerobic chamber 203 to support and stabilize the anaerobic chamber 202 in place.

Figure 20:
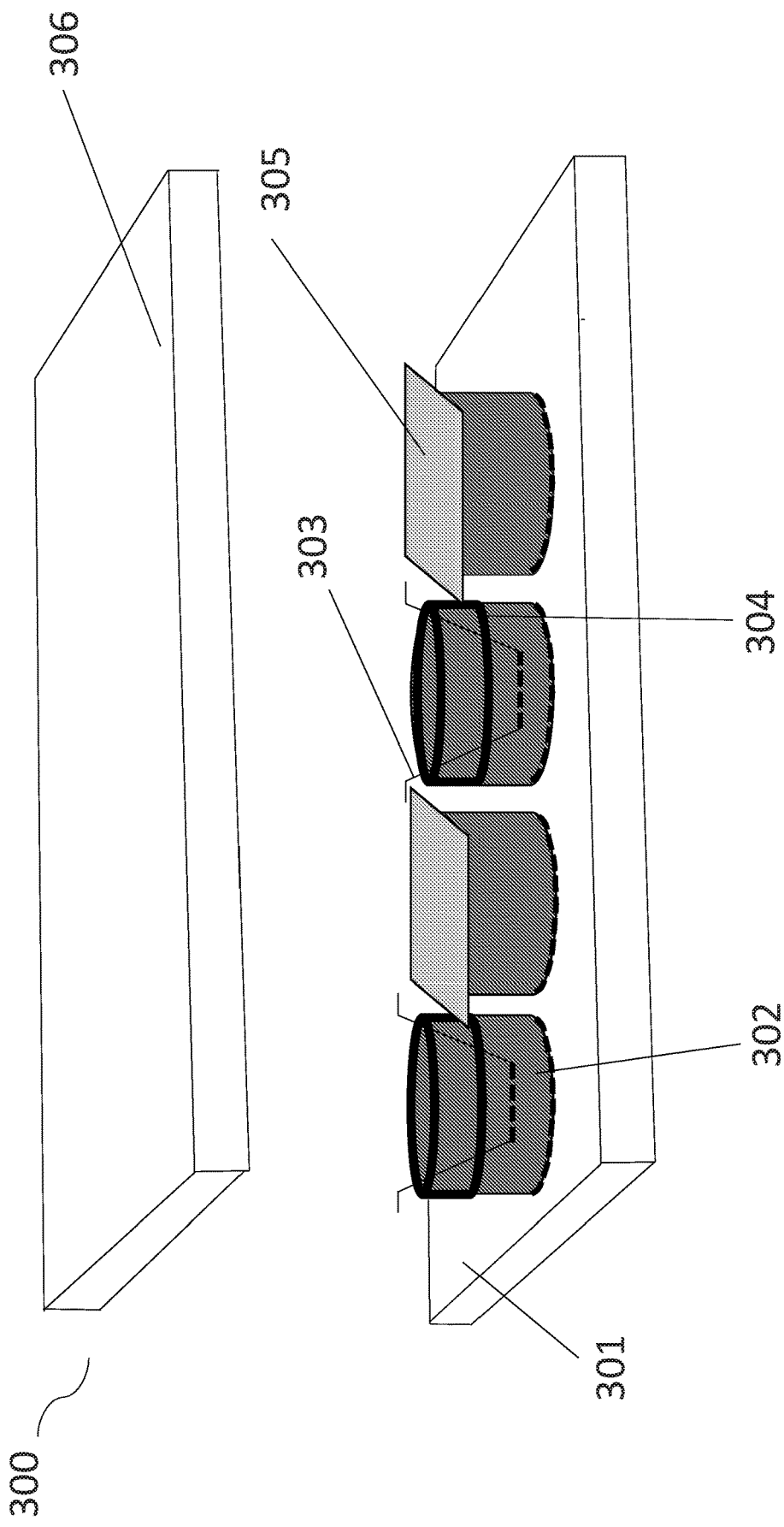
FIG. 20 shows one embodiment of assembled anaerobic and aerobic chambers.

FIG. 20 illustrates the assembled anaerobic co-culturing system 300. In specific embodiments, a multi well plate 301 comprises the gas permeable aerobic chambers 302. The gas permeable anaerobic chamber 303 is fitted with an external gasket 304 that is inserted into the aerobic chamber 302. The multi well plate 301 comprising aerobic chambers 302 is further sealed with a two-sided adhesive 305 affixed onto the top surface of the aerobic chamber 302. In specific embodiments, the two-sided adhesive 305 seals the aerobic chambers 302 not in use and assists in the regulation gas circulation, wherein the aerobic chambers 302 are receiving gas from its gas permeable base. In another specific embodiment, the multi well plate comprising aerobic chambers 301 has a lid 306 mounted to the assembled anaerobic co-culturing system 300. The lid 306 may or may not be comprised of Polysulfone, for example. In particular embodiments, the two-sided adhesive is different on each side: one side may specifically bind silicone/rubber while the other side specifically binds acrylic/plastic; such a differential allows a rubber gasket to adhere to a plastic plate effectively.

Figure 21:
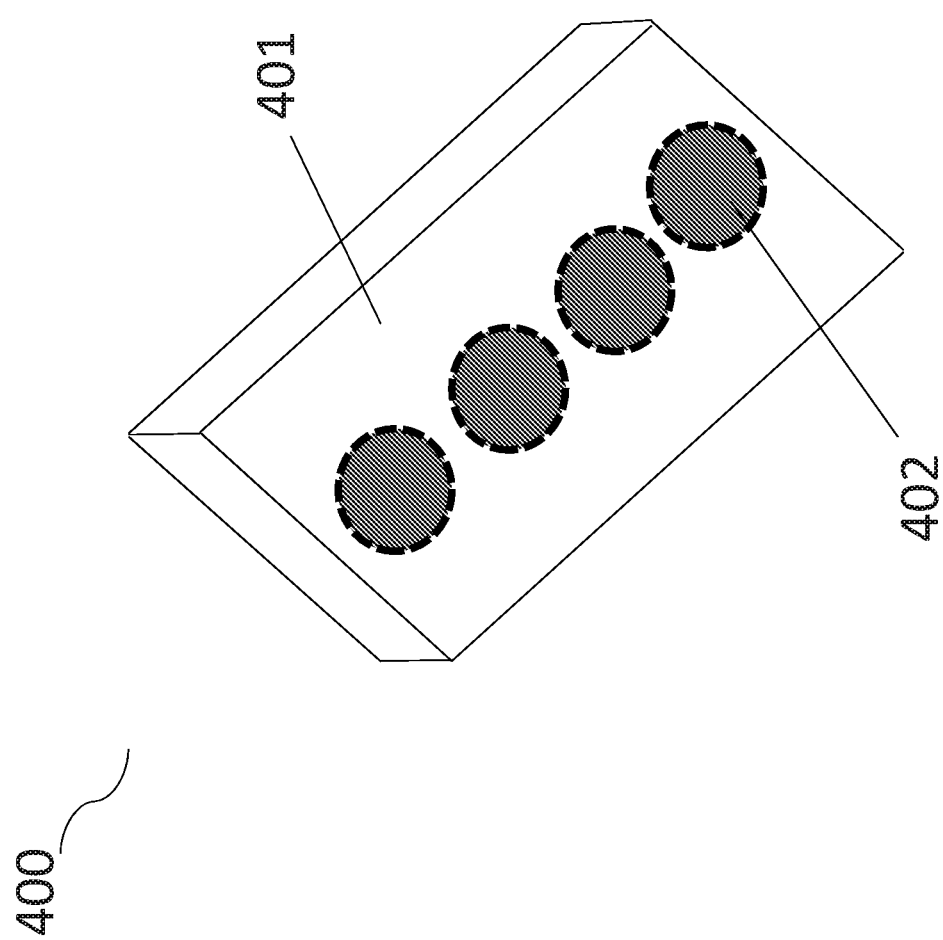
FIG. 21 provides one embodiment of a bottom-view of a multi well plate comprising aerobic chambers with gas permeable bases.

In FIG. 21, an embodiment of the anaerobic co-culturing system 400 is provided. The bottom of the multi well plate 401 comprises gas permeable bases 402 within the aerobic chambers. In specific embodiments, the aerobic chamber with a gas permeable base receives gas from the bottom of the multi-well plate 401 comprising aerobic chambers.

B. Enteroid Cultures

Embodiments of anaerobic enteroid cultivation systems of the present disclosure utilize environments that mimic the natural physiological normal or diseased human intestine. In particular embodiments, the present cultivation system employs human intestinal enteroids. As used herein, an enteroid may be a three-dimensional culture system that originate from stem cells derived from intestinal crypts and obtained from human surgical specimens, autopsy specimens, and/or endoscopic biopsies. The skilled artisan recognizes the term "organoid" may be used interchangeably in the art with the term "enteroid" in the literature. As used herein, enteroids are made from intestinal specimens, such as those obtained from biopsy, autopsy specimens, surgical specimens, and/or stem cell lines or induced pluripotent stem cells. The enteroids of the system may be generated from cells in a species-specific manner when considering the application of its use: when testing for human applications, the enteroids may be derived from human cells; when testing for dog applications the enteroids may be derived from dog cells; and so forth.

In particular embodiments, the enteroids are provided to, such as generated within, a chamber that is an aerobic chamber. The enteroids may be generated by any suitable means, but in specific embodiments they are differentiated for at least 4 days but no more than 7 days, for example. The range of days may be 4-7, 4-6, 4-5, 5-7, 5-6, or 6-7 days, for example. Prior to use in the system, the enteroids may or may not be sampled or otherwise tested to confirm suitability for their use. For example, following equilibration in the system (for example, about 2 hours at about 5% oxygen), the enteroids may be tested by transepithelial/transendothelial electrical resistance, certain histology, levels of one or more certain RNAs, and/or survival. In some cases, the microbe(s) are added following equilibration and testing.

In particular cases, the culture system comprises enteroids that are jejunal, duodenal, ileal, or a combination thereof. In specific embodiments, the enteroids are crypt-derived enteroids. In at least some cases, the starting material for the enteroids is one or more biopsies from a mammal. In particular embodiments, the tissue comprises stem cells that have the capacity for regenerating and differentiating into the specific cell types that make up the intestinal epithelium. In specific embodiments, the stem cells are isolated from intestinal crypts. In certain embodiments, the source of tissue for the generation of the enteroids is small intestine, colon, stomach, or a combination thereof. The tissue may come from surgically resected intestinal tissues, endoscopic biopsies, autopsy specimens, and so forth.

In at least some cases, the cultures are generated upon exposure of intestinal cells of isolated crypts that contain stem cells or a combination of stem cells and Paneth cells to one or more growth factors. Specific examples of growth factors include Wnt3A, nicotinamide, R-spondin-1, noggin, epidermal growth factor (EGF), gastrin, laminin-□□1, laminin-□2, an inhibitor of Alk (such as A-83-01), an inhibitor of p38 (such as SB202190), fibroblast growth factor 10, or a combination thereof. The media for the generation and maintenance of the cultures may comprise standard basal media or media comprising suitable levels of one or more growth factors (such as EGF, noggin, R-spondin, Wnt3A, nicotinamide, SB202190, and/or acetylcysteine).

Examples of methods of generating enteroids for use in cultivation systems of the disclosure may be as follows: intestinal fragments or biopsy intestinal sample fragments are obtained or generated and washed with buffer (such as PBS) until the supernatant is clear, incubated in a buffer that comprises EDTA, and then the fragments are vigorously resuspended to isolate intestinal crypts. Following a resuspension/sedimentation procedure, supernatants comprising crypts are subject to procedures to separate crypts into single cells. These crypts are expanded as 3D cultures and then embedded in a gelatinous protein mixture (such as Matrigel or hydrogels), followed by polymerization. After further expansion in growth media, the cells in the three-dimensional cultures are dissociated and may be plated onto monolayers on top of a thin coating of Matrigel or collagen or other such substrates for forming monolayer cultures. Cultures in either 3D or monolayer (2D) format can be differentiated by withdrawal of Wnt3a, for example, which then results in the appearance of all the cells in the epithelium being produced. Both non-differentiated and differentiated cultures can be infected, in certain embodiments, but in particular cases only differentiated cultures may be infected.

Enteroids may be transduced with viral vectors (such as adenovirus, lentivirus, or adeno-associated virus, for example); when lentivirus or adeno-associated viruses are utilized, they can permanently express one or more genes. CRISPR/Cas9 or CRISPRi may alternatively be employed to genetically manipulate the cultures to express one or more genes. The cells of the enteroids may be transduced to overexpress molecule(s) in pathways identified to be critical for virus entry or replication. Pathways to be targeted may include ESCRT, autophagy, calcium mobilization, lipid biogenesis and cholesterol metabolism, and the unfolded protein response. A variety of biosensors can also be expressed that can detect by fluorescent imaging or flow cytometry a cell property that changes after infection. These modified cell lines may be established cells that currently do not support HuNoV replication in the presence of bile or bile acids (e.g., HEK, CaCo-2, HT29, MA104, Vero, as examples). In addition, permissive cells within the enteroid cultures may be identified and immortalized by expressing molecules such as telomerase or SV40 T antigen to develop homogeneous epithelial cell lines that support virus replication and can be expanded easily and robustly. Examples of some specific proteins in the pathways above for overexpression are Rab1, dynamin, VAP-1, VAMP1, ALIX, FXR, SHP and PPAR gamma, or silencing HMG-COA synthase and ACAT.

C. Microbe Preparation or Functional Component(s) Thereof

In particular embodiments, the anaerobic cultivation system of the present disclosure utilizes one or more microbes or functionally active fraction(s) or component(s) thereof. The purpose of the one or more microbes in the system is to approximate the physiological environment of a gut in vivo. The combination of the enteroids with one or more microbes recreates the ex vivo co-culture systems of the present disclosure.

The present systems may be used for culturing any kind of microbe with the enteroids to reproduce or approximate an in vivo gut. In doing so, the system provides a means for testing or characterizing conditions associated with a gut-microbe interaction. Such characterization of the interaction could lead to testing one or more therapies for a disease state that may or may not be associated with that particular gut-microbe interaction. In specific embodiments, the system is re-usable. For example, one may re-use the system following suitable treatment of the system with appropriate antibiotic(s) to remove the previous microbe(s).

In particular embodiments, one or more microbes are placed into the system because they are part of a healthy gut environment, and it is desired to be analyzed as such. In some embodiments, one or more microbes are placed into the system because they are part of a diseased gut environment, and they are desired to be analyzed as such. In certain embodiments, one or more microbes are therapeutic for an individual, and such a microbe is placed into an established system already having one or more microbes that recreate either a healthy gut environment (for example, to test toxicity of the therapy on the healthy tissue) or already having one or more microbes that recreate a diseased gut environment (for example for testing therapeutic efficacy on the diseased tissue).

In specific embodiments, the source of the microbe may or may not be the same source as the cells that generate the enteroid. The microbe may be bacteria, viruses, fungi, or a combination thereof. In some embodiments, a source fungi for cultivation includes human clinical samples, samples from other mammals (e.g. primates, bovine, canine, feline, porcine). Examples of gut fungi include at least *Wickerhamomyces, Candida, Cyberlindnera, Debaryomyces. Sporopachydermia, Eurotiales*, and a mixture thereof.

In a specific example, commensal species (as examples *B. thetaiotaomicron* and *L. blautia*) are cultivated from healthy human microbiome(s) for subsequent use in the system of the disclosure. Bacterial populations may be kept consistent by utilizing a continuous flow bio-reactor array system. The bioreactors are inoculated with one or more bacterial isolates and allowed to equilibrate for an extended period. After equilibrium, the flow rate is maintained at 1.875 ml/hr for a total of eight hours total. Prior to culturing, a small volume of the bacterial culture is collected, diluted, and plated onto a bioreactor media agar plate (*B. thetaiotaomicron*) or GM-17 agar plates (*L. blautia*) for twenty-four to forty-eight hours to determine viability and CFU/ml concentration.

In some embodiments, a source virus for cultivation includes human clinical samples, samples from other mammals (e.g., primates, bovine, canine, feline, porcine, canine) environmental surfaces, foods, liquids, and other environmental surfaces (e.g., sewage, sludge).

The cultivating systems, methods, and/or compositions of the present disclosure may be used in any strain, genotype, or variant of any virus that infects the gastrointestinal tract of a mammal. In specific embodiments, the mammal is a human, bovine, pig, primate, feline, or canine.

IV. Methods of Use of the Anaerobic Enteric Cultivation System

The anaerobic co-culturing system of the present disclosure recapitulates the physiological environment of the gastrointestinal (GI) tract. Studies have shown altered phenotypes and gene expression of gut tissues compared to those cultured at physiological oxygen levels. Thus, being able to model the host gut tissue-microbe interactions under biologically relevant oxygen conditions is useful to understanding host gut tissue-microbe interactions and to develop and/or better understand therapies that strive to restore this interaction.

The anaerobic co-culturing system of the present disclosure may be used for research purposes, for therapy or diagnostic identification purposes, for identifying host-microbe relationships, and so forth. In particular embodiments, one can cultivate any microbe (e.g. bacteria, virus or fungi) for their robust replication and passaging to study and/or test such microbes in relation to worldwide disease. One can use the systems to characterize cellular processes and pathways to obtain information on targets exploited by the host-microbe interaction for physiological responses and/or pathogenesis. One can also assess methods and/or compositions (such as therapies and/or diet) that can affect the beneficial host-microbe interaction and such activity can be measured for effectiveness of restoring a normal host-microbe relationship. In addition, one can also cultivate the microbes along with the host gut tissue to understand the pathological phenotype of the host gut tissue. In a specific embodiment, the cultivation system provides for the development of a therapy to restore the normal host-microbe relationship in the intestinal tract.

Using the anaerobic co-culturing system of the present disclosure, one can also cultivate the anaerobic microbes along with host gut tissue seeded as monolayers, also referred to as an enteroid, onto a gas permeable support. To better understand host-microbe interactions in GI tract, enteroids can be co-cultured with microbes in an environment that biologically replicates the oxygen requirements of the GI tract. In additional embodiments, one can cultivate the anaerobic microbes and/or enteroids in a physiologically relevant oxygen environment to improve reproducibility of studies and better determine therapy efficacy. In specific embodiments of the methods, the effects of cultivating microbes and enteroids in a physiologically relevant oxygen environment produced a robust gene expression profile and cell barrier integrity.

In particular embodiments, the enteroid cultures are plated in a monolayer prior to exposure with a microbe and/or a therapy. The enteroid monolayers comprise differentiated cells. The combination of the microbe and the enteroid culture may occur prior to, during, and/or after exposure of the system.

In some embodiments, the cultivation system provides for the development of a therapy that can provide relief for individuals diagnosed with enteric disease. In specific embodiments of the methods, the effects of the therapy restore cell barrier integrity and/or mitigate hypoxia induced gene expression in the GI tract.

In specific embodiments, a sample from an individual that is known to have or that is suspected of having enteric disease or is suspected of having been exposed to an environment causing enteric disease is subjected to cultivation systems and/or methods of the disclosure.

An individual whose sample may be subjected to methods of the disclosure include an individual that may or may not be showing symptoms (e.g. diarrhea, abdominal pain, abdominal cramping, fever, headaches, muscle pain, infection, and so forth) of enteric disease that has or has not been known to be exposed to an environment capable of inducing and/or have a genetic disposition for enteric disease development.

Embodiments of the disclosure concern methods, systems, and/or compositions for culturing any microbe that is present in the GI tract of a mammal, including a human, pig, bovine, primate, dog, or cat, for example. In specific embodiments, the microbe is a bacteria, including Bacteriodetes, Firmicutes, Actinobacteria, Proteobacteria, and Verrucomicrobia. In some embodiments the microbe is a virus, including Rotaviruse, "Norwalk-like" viruse, Adenoviruse, Astroviruse, "Sappro-like" viruse, Toroviruse, Coronaviruse, Picornavirue, and Herpesvirus. In other embodiments the microbe is a fungi; including *Ascomycota, Basidiomycota, Mucoromycota, Saccharomyces, Malassezia, Candida, Cyberlindnera, Penicillium, Cladosporium, Aspergillus, Agaricus, Fusarium, Pichia, Debaryomyces, Galactomyces, Altemaria*, and *Clavispora*.

In certain embodiments, there are methods of providing the systems of the disclosure an effective amount of a therapy to determine its efficacy. This new enteroid anaerobic co-culturing system will allow (i) the determination of whether a microbe(s) s presence in the GI tract is beneficial or pathogenic; (ii) evaluation of host-microbe interactions, functions, and/or biologically relevant responses pertaining to said interaction; (iii) discovery and elucidation of the molecular mechanisms that regulate host-microbe interaction; (iv) detection of a genetic profile that is known or unknown to be related to enteric disease; (v) providing an individual with personalized medicine methodology to evaluate the effectiveness of treatments.

V. Methods of Manufacture

The anaerobic culturing systems, methods, and/or compositions of the present disclosure may be used for any strain, genotype, or variant of any microbe capable of infecting the gastrointestinal tract of a mammal. In specific embodiments, the mammal is human, bovine, pig, primate, horse, dog, or cat.

In certain manufacturing methods, the apparatus of the system may be prepared. Other method steps may include one or more of the following, in no particular order: (1) isolation and preparation of the one or more microbes to be provided to the system; (2) obtaining gut tissue from which enteroids are prepared; (3) preparation of enteroids; (4) establishing the proper oxygen levels for the anaerobic chamber, aerobic chamber, or both; (5) determining a proper oxygen level for the anaerobic chamber, aerobic chamber, or both; and optionally (6) obtaining or preparing a therapy to be tested; and (7) testing the therapy to be tested.

In some embodiments, the microbes are prepared, such as isolated and perhaps cultivated, prior to placement into the system. A source of the microbe for cultivation may include from human or from other mammals (e.g., pig, primate, canine, feline, bovine). As part of the isolation and preparation, the identity of the microbe(s) may be confirmed, such as by standard methods.

In at least particular embodiments, the enteroid cultures are plated or generated in a monolayer prior to providing the microbe(s) to the system. In specific embodiments, the monolayer comprises differentiated cells initially, and under the right conditions and for a suitable amount of time the differentiated cells become enteroids. In some cases, a therapy will be combined with the enteroid culture prior to, during, and/or after exposure of the system to the microorganism. The therapy may be a known drug that is being tested for efficacy for a particular individual, or the therapy may in fact be a candidate therapy being tested for efficacy as part of drug development.

In at least some cases, the therapy-treated enteroid cultures are monitored by assaying the cell barrier integrity and/or gene expression in the enteroids that are plated in a monolayer. The cell barrier integrity and/or gene expression can be monitored by polymerase chain reaction (including RT-PCR), hybridization (such as dot blot hybridization or in situ hybridization), and/or sequencing, or a combination thereof.

In at least some cases, the therapy-treated enteroid cultures are monitored by assaying particular protein levels and/or identity, and/or cytopathic changes (through standard histology methods) in the enteroids that are plated in the monolayer.

Methods of manufacture may include exposure of microbes to the system at no less than 30 minutes, 45 minutes, 1 hr, 2 hrs, 3 hrs, etc. after establishment of proper oxygen levels in the anaerobic and aerobic chambers of the system.

VI. Kits of the Disclosure

Any of the systems or component(s) thereof encompassed herein may be comprised in a kit. In a non-limiting example, the kit may comprise an anerobic chamber, an aerobic chamber, and/or a gas adjustable chamber or any component of any of the chambers or system. The kit may comprise one or more permeable supports or analogous components. Additionally, or alternatively the kit may comprise one or more microbes (sufficiently stored); one or more media, buffers, and so forth; and or one or more therapeutic compounds. The kit may also include a means to block openings of a permeable support, such as two-sided adhesive tape.

For the biological materials of the kit, the components may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present disclosure also will typically include a means for containing any reagent container(s) in close confinement for commercial sale. Such containers may include injection or blow-molded plastic containers into which the desired vials are retained.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Enteroid-Anaerobe Co-Culture Assembly (EACC)

Mechanistic investigations of host-microbe interactions in the human gut, both beneficial and pathogenic, are severely limited by current co-culture model systems. There are two principle challenges to in vitro modeling of host-microbe interactions in the gut. First, the intestinal epithelium is oxygen dependent while many gut bacteria are facultative or obligate anaerobes. This creates an incredibly steep oxygen gradient across the epithelial monolayer. Second, the intestinal epithelium is in a state of chronic low-grade hypoxia, which is then dramatically exacerbated in chronic inflammatory conditions such as Inflammatory Bowel Disease (IBD). Hypoxia alters the intestinal epithelium in a variety of ways that impact bacterial invasion and host-microbe interactions. Thus, being able to model host-commensal interactions under dynamic oxygen conditions is critical to understanding host-pathogen interactions in the human gut. There are several technologies currently available to facilitate such experiments, each with technological, economical, and/or accessibility limitations that make these systems difficult or unpalatable to adopt (table below).

| System | IP protection | Cost | Assembly Materials | Cell Type | O2 Control | Direct Contact | Mucus Layer | Host-Microbe co-culture time | Flow | Co-culture with anaerobic bacteria |
|---|---|---|---|---|---|---|---|---|---|---|
| HMI ™ module | Yes | High | Complex | Caco-2 | Yes | No | Yes (artificially added) | Up to 48 h | Fluid | *F. prausnitzii* |
| HoxBan | No | Low | Simple | Caco-2 | No | Yes | Yes (artificially added) | Up to 36 h | Static | *F. prausnitzii* |
| gut-on-a-chip | Yes | High | Complex | Caco-2 | Yes | Yes | Yes | 1-2 weeks | Fluid | Not described |
| HuMiX | Yes | High | Complex | Caco-2 | Yes | No | Yes | 24 h | Fluid | Bacteroides *caccae* |
| EACC System | Yes | Low | Simple | Enteroids, Caco-2 | Yes | Yes | Yes | 8-24 hr | Static | *B. theta, Blautia* sp. |

Thus, there is a critical need for a cost-effective, easy to assemble system to model host-anaerobe interactions under physiologically relevant oxygen conditions. To address this gap in methodology, the inventors developed a simple system for co-culturing obligate anaerobic bacteria with human intestinal enteroid monolayers under variable oxygen conditions (EACC system). Briefly, 3D enteroids are seeded as monolayers in permeable supports, such as Transwells®, for example. These slip into modified gaskets which are then sealed in place, using a special double-sided adhesive tape, on a 24-well plate with a gas-permeable base. Gas is pumped from an external tank through the base of the plate to feed the basolateral side of monolayer. The entire apparatus is kept in an anaerobic chamber so that anaerobic bacteria can be cultured on the apical surface in standard anaerobic conditions. This allows the user to control the amount of oxygen supplied to enteroid monolayers during co-culture. Unlike other technologies, the EACC system has been developed to fit the standard workflow of an enteroid culture laboratory but can also be employed for standard cell culture lineages like Caco-2. Unlike the HMI module and the HuMiX system, EACC allows for direct contact between microbe and epithelium with no artificially added mucus layers or permeable barriers, thereby reflecting a more physiologically relevant interaction. Although the gut-on-a-chip system also allows for direct contact, it currently does not support the growth of obligate anaerobes. Importantly, the EACC system can be assembled by the user quickly, with minimal instruction, using existing commercially-available products and common laboratory equipment.

Example 2

Enteroid-Anaerobe Co-Culture ASSEMBLY (EACC)

Figure 1B:
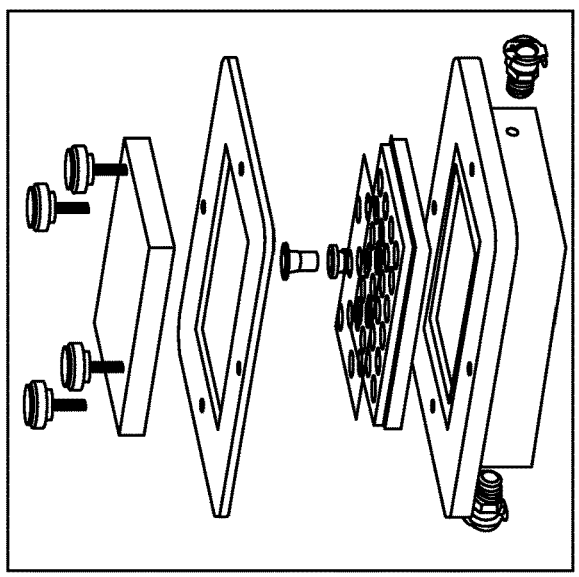
FIG. 1B illustrates one embodiment of the system showing different components including the lid, adapter, anaerobic chamber, gasket, adhesive, aerobic chamber, and gas adjustable chamber.
Figure 1A:
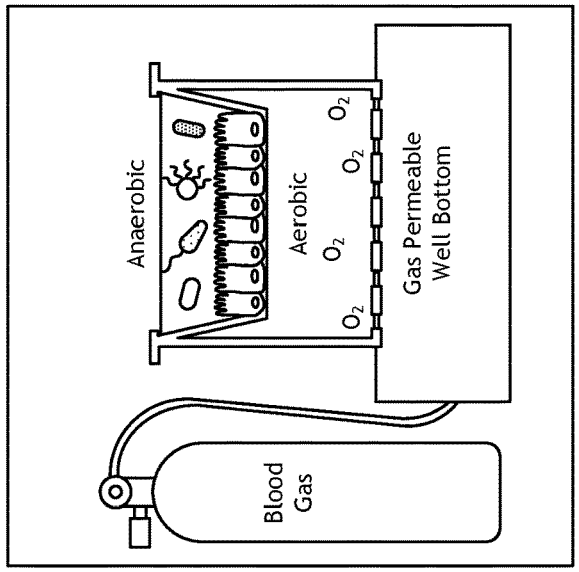
In FIG. 1A there is an illustration of one embodiment of the system including an anerobic chamber, an aerobic chamber, and a gas-permeable well bottom linked to a blood gas source.

To address deficiencies in the art, the inventors developed a simple, cost-effective method for co-culturing obligate anaerobic bacteria with human intestinal enteroid monolayers under variable oxygen conditions. In this system, referred to as EACC and as illustrated in FIGS. 1A, 1B, and 1C, enteroids are seeded as monolayers in Transwells®. These slip into modified gaskets that are then sealed in place with a two-sided (gas impermeable) adhesive on a 24-well plate with a gas-permeable base. Gas is pumped from an external tank with defined gas levels through the base of the plate to diffuse into the media and feed the basolateral side of monolayer. In specific embodiments, the entire apparatus is housed in an anaerobic chamber so that anaerobic bacteria can be cultured on the apical surface in standard anaerobic conditions. This allows control of the amount of oxygen supplied to the enteroid monolayers during co-culture. This allows the modeling of host-anaerobe interactions during physiological hypoxia.

FIG. 1B illustrates the system utilizing an adapter that may sit on the lid of the 24 well plate to clamp it down; such an adapter ensures a strong seal between the plate and the console, in specific embodiments.

FIG. 1D provides an example of the set-up and general assembly. Although the gas permeable plates come with a standard disposable lid, the modified gaskets raise the plate's total height. As a result, the inventors initially encountered issues with apical media evaporation and external contamination. However, after some experimentation with various materials, an autoclavable lid was designed.

FIG. 2 shows that predictive modeling of enteroid oxygen consumption establishes operational limits of the co-culture system. By tracking oxygen levels over time, one can predict the oxygen consumption of monolayers and use that to determine the working oxygen range of the system that would allow both microbes and human cells to survive. FIG. 2A shows two oxygen gradient models of the co-culture well. The left of FIG. 2A shows oxygen consumption in the presence of an enteroid monolayer. The enteroids consume enough residual basolateral oxygen to prevent an apical leak resulting in an effectively anaerobic apical compartment. On the right of FIG. 2A is the same gradient but without enteroids to consume the residual oxygen; under these conditions, anaerobic bacteria would not be able to survive. Importantly, one can use these models to determine the point at which the system reaches equilibrium. In FIG. 2B, one can see an initial spike of oxygenation, because these enteroids are provided fresh media and transferred from ambient oxygen conditions to the co-culture system. However, all locations within the Transwell® reach near-zero levels at approximately 2 hours. Thus, in specific embodiments, the oxygen-sensitive microbes may be added after the 2 hour mark. In particular embodiments of the system, the apical compartment reaches equilibrium 2 hours after set-up and an operating range may be about 2-10% $O_2$.

Figure 3:
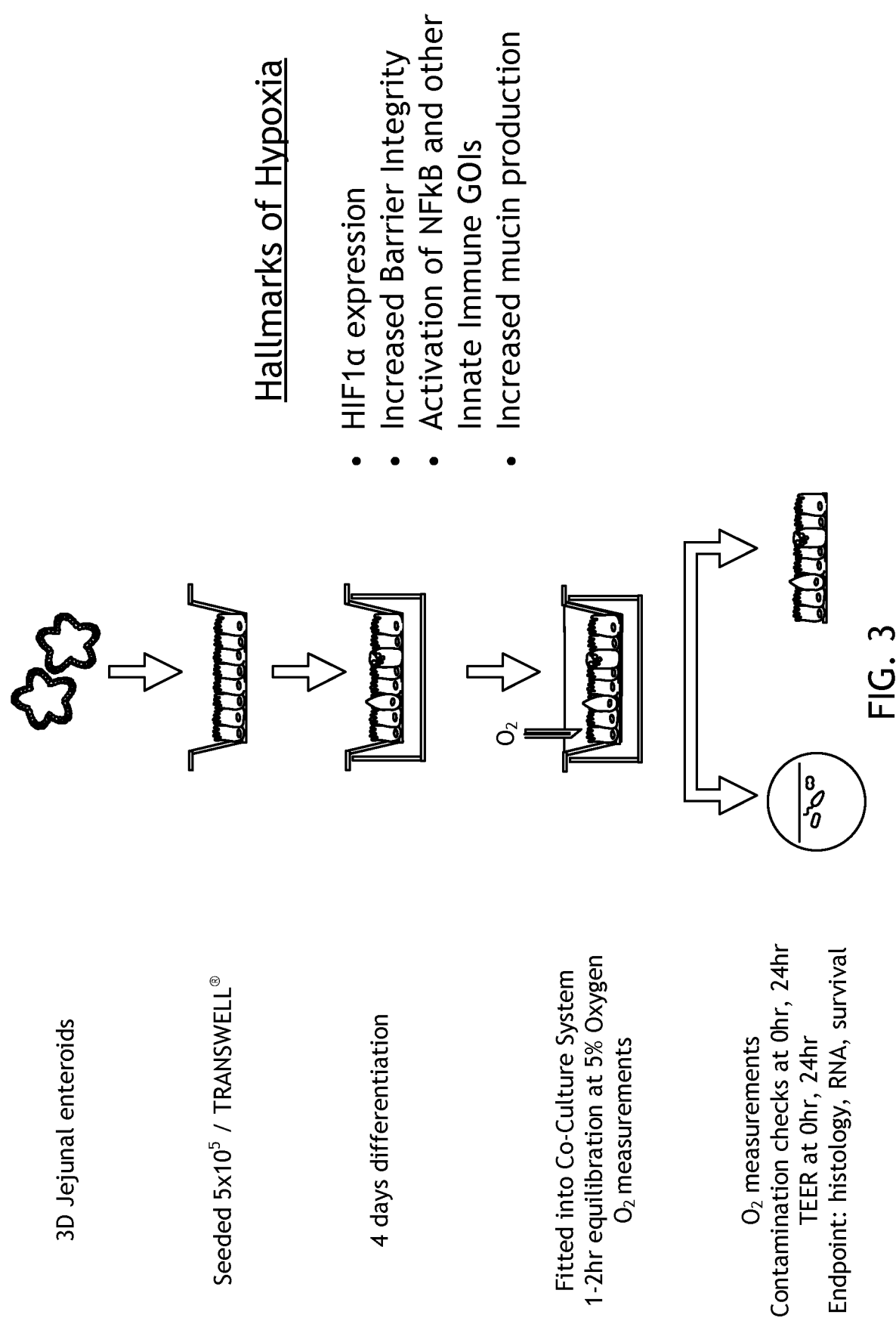
FIG. 3 illustrates one embodiment of experimental design and manufacture of the system.

FIG. 3 illustrates one embodiment of a development design for the system. The presence of hypoxia may be tested by one or more characteristics, such as HIF1α expression; increased barrier integrity; activation of NFkB and other innate immune genes of interest; and/or increased mucin production.

FIG. 4 demonstrates that the EACC system recapitulates in-vivo conditions. Using a trypan blue dye exclusion assay to assess survival, it is determined that there is no difference in survival between enteroid monolayers in standard incubator conditions and those exposed to the system for 24 hours. The enteroid monolayers are polarized (villin) and have normal morphology (alcian).

Figure 5:
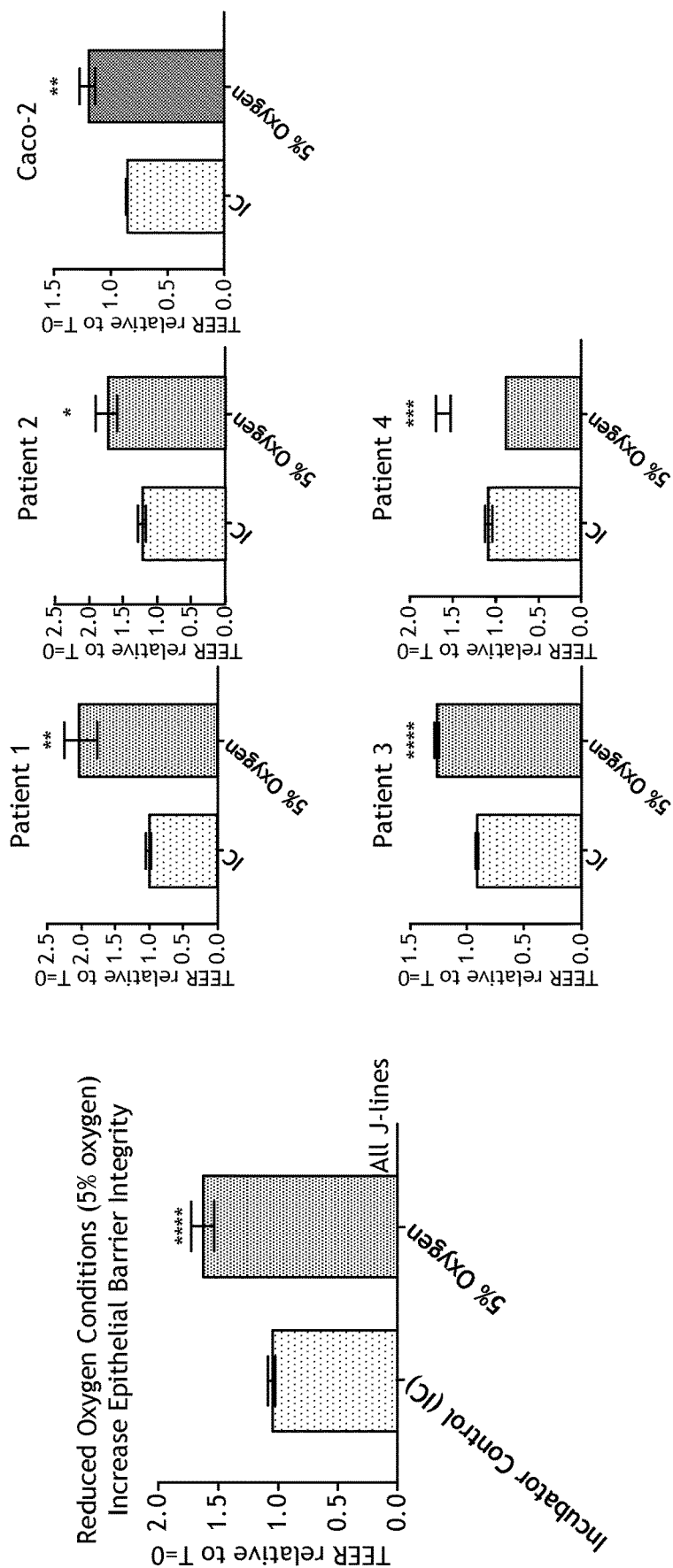
FIG. 5 demonstrates that physiological hypoxia increases epithelial barrier integrity.

FIG. 5 shows that physiological hypoxia increases epithelial barrier integrity. Reduced oxygen consistently and reproducibly improves barrier integrity, as measured by TEER from 4 separate enteroid donors. One would expect such an outcome in an hypoxic epithelium. This was also tested in a traditional cell line, Caco-2, and a similar outcome was observed.

Figure 6A:
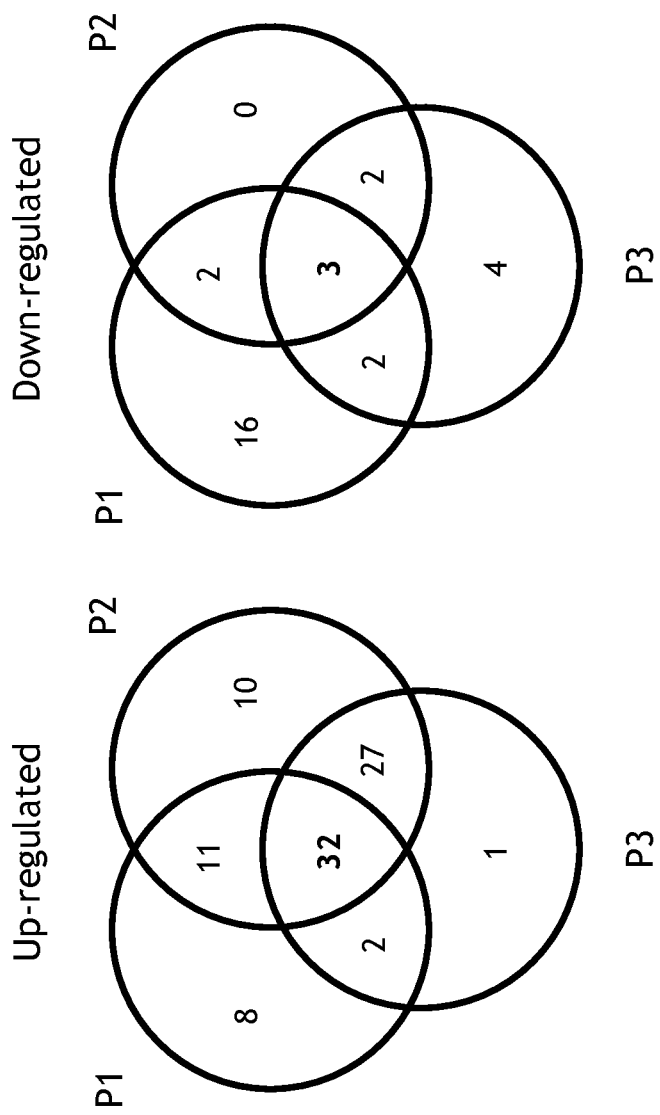
FIG. 6 demonstrates gene expression under physioxia conditions.
Figure 6B:
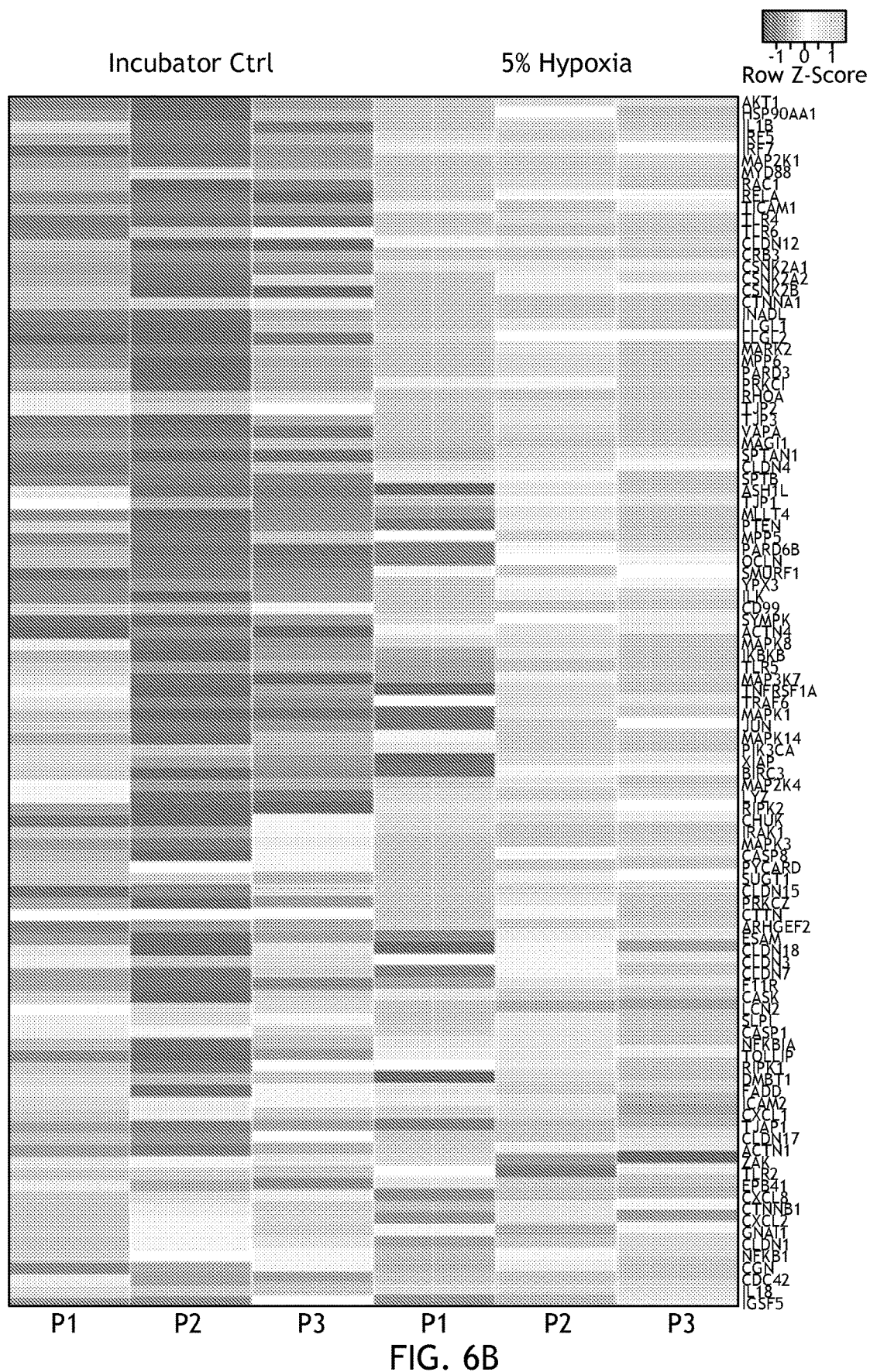

Studies have shown that low $O_2$ conditions are critical for the constitutive expression of innate immune factors and the expression of genes that enable epithelial cells to function as an effective barrier. FIG. 6 shows the results of gene expression in physioxia.

FIG. 6 shows gene expression in physioxia. Studies have shown that low $O_2$ conditions are critical for the constitutive expression of innate immune factors and the expression of genes that enable epithelial cells to function as an effective barrier. To determine if this was recapitulated within a system of the disclosure, the inventors surveyed 106 tight junction and innate anti-microbial response genes. The heat map shown in FIG. 6 illustrates the significant changes in gene expression of both epithelial barrier integrity genes and anti-microbial immune response genes during physiological hypoxia.

Figure 7A:
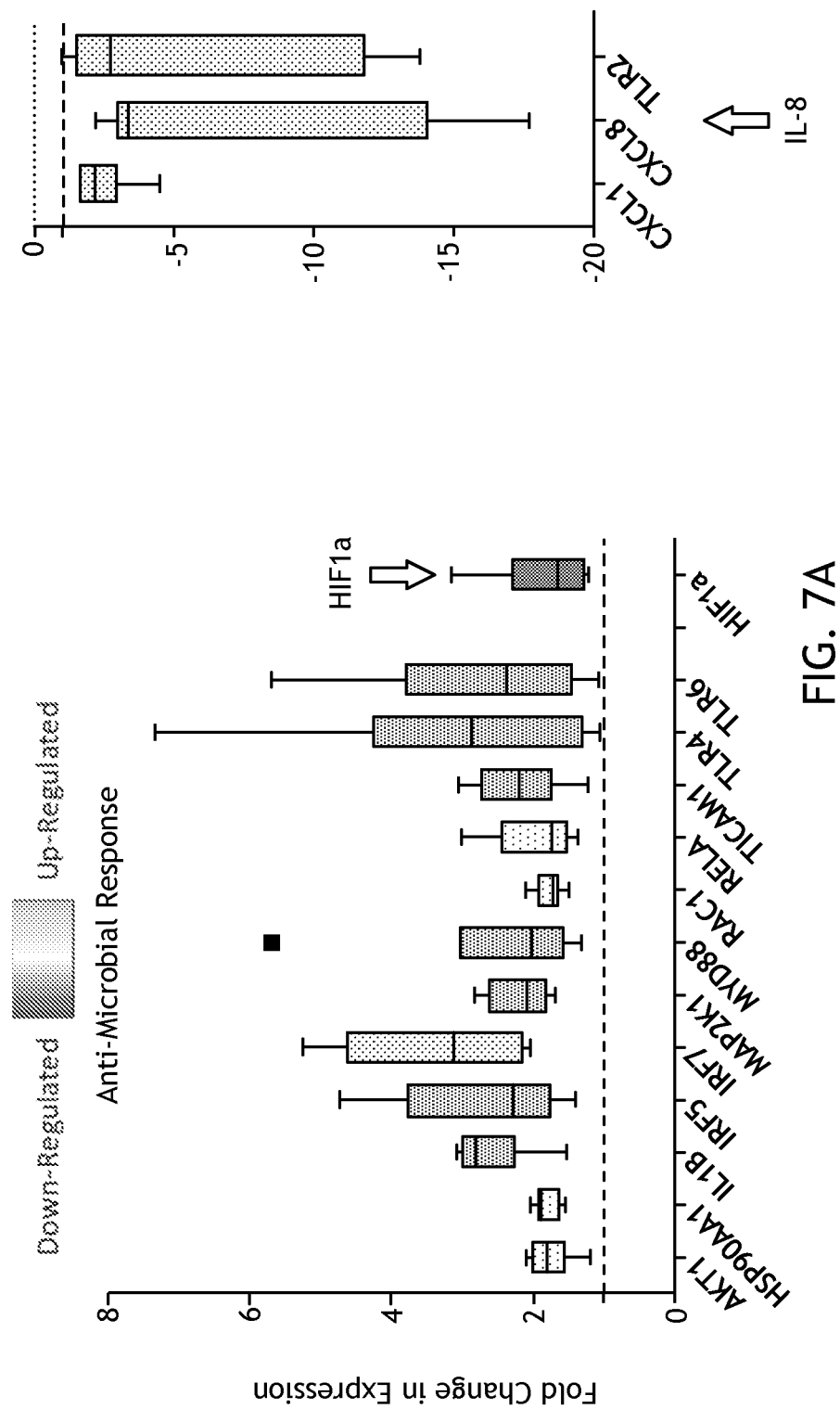
FIG. 7 shows gene expression under physioxia conditions including downregulation of interleukin (IL)-8, an inflammatory cytokine sometimes associated with hyperoxia and significantly produced by enteroid lines.
Figure 7B:
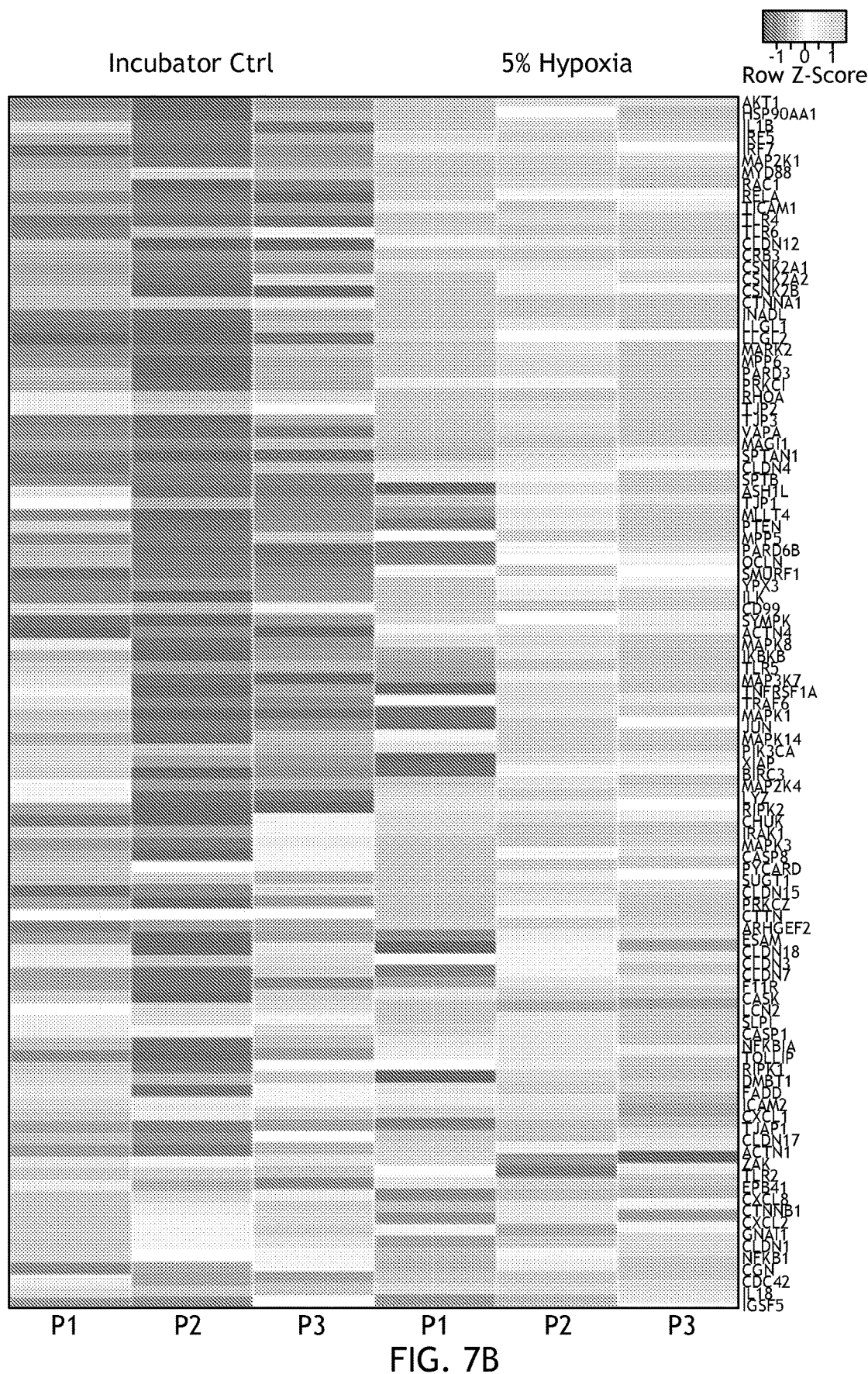

By looking at pathway analysis, the inventors also found activation of NFkB and positive regulation of nitric oxide production, both of which are involved in tempering hypoxic activities in the cell. Of the genes analyzed, 32 were significantly upregulated in 5% physiological hypoxia relative to standard incubator conditions, and 3 were significantly down-regulated across all cell lines. Interestingly, one of those genes was IL-8 (FIG. 7), an inflammatory cytokine sometimes associated with hyperoxia and produced voluminously by the enteroid lines. Therefore, one can generally reproduce hypoxia in the system.

In one embodiment, the system is used upon the introduction of anaerobic bacteria. Bacteroidetes and Firmicutes of the family Lachnospiraceae are the most abundantly represented phyla in the human gut. To test the EACC system, the inventors chose two anaerobic commensals from these phyla and co-cultured them with human jejunal enteroid monolayers under 5% basolateral oxygen (FIG. 8). *B. thetaiotaomicron* is a gram-negative, acetate-producing nanoanaerobe from the Bacteroidetes phylum. *Blautia* is a gram-positive, lactate- and acetate-producing obligate anaerobe associated with reduced death from graft-vs-host disease.

FIG. 9 demonstrates that the EACC System supports enteroid-nanoanaerobe co-culture for at least 24 hours for *B. theta*. Here, the experimental approach was similar to that of earlier hypoxic experiments. However, in co-culture experiments, following 2 hours of equilibration within the anaerobic chamber, approximately $3 \times 10^4$ bacteria were spiked into the apical compartment.

Bacteria were co-cultured in the presence and in the absence of enteroid monolayers to validate the model that enteroids consume residual oxygen and lead to an anaerobic luminal compartment. In FIG. 9, one can see that the EACC system supports the growth of the nanoanaerobe *B. thetaiotaomicron*, which first adheres to the epithelium but by 24 hours is pushed away (presumably by mucus and defensins). *B. theta* demonstrates robust growth for at least 24 hours as measured by colony forming units (CFU/mL). In addition, co-culture reduced transepithelial resistance in a patient-specific manner.

Figure 10:
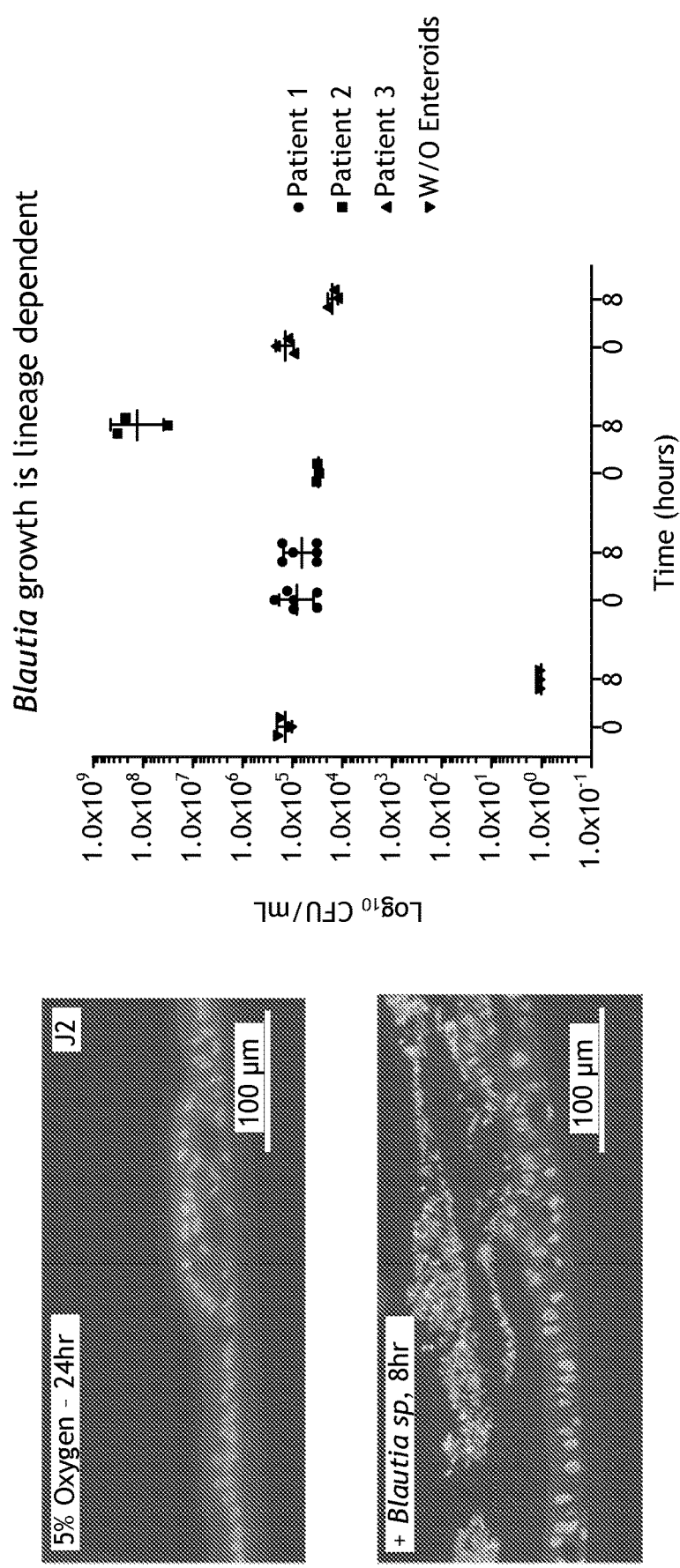
FIG. 10 shows with the EACC system that enteroid-anaerobe co-culture is supported for at least 8 hours, as demonstrated by *Blautia* sp. being lineage dependent.

The EACC system also supports the survival and growth of *Blautia* spp., which has a comparatively fast doubling time and is not able to tolerate any residual oxygen. As shown in FIG. 10, without enteroids to consume luminal oxygen, *Blautia* dies. The survival and growth of *Blautia* is dependent on patient lineage.

Figure 11:
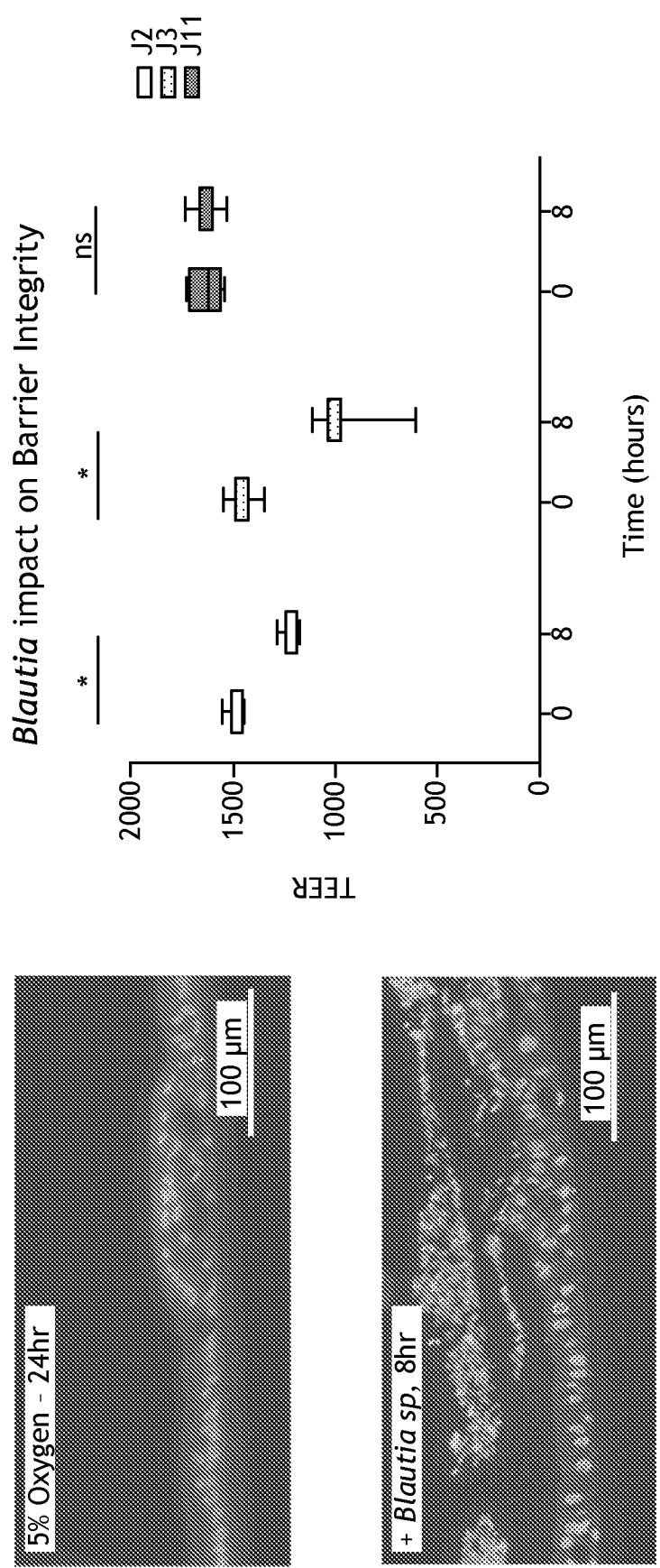
FIG. 11 demonstrates that the EACC System supports enteroid-anaerobe co-culture for *Blautia* sp. for at least 8 hours and as shown by barrier integrity.

FIG. 11 shows that, similar to *B. thetaiotaomicron* co-culture, *Blautia* affects transepithelial resistance in a patient-specific manner.

Figure 12A:
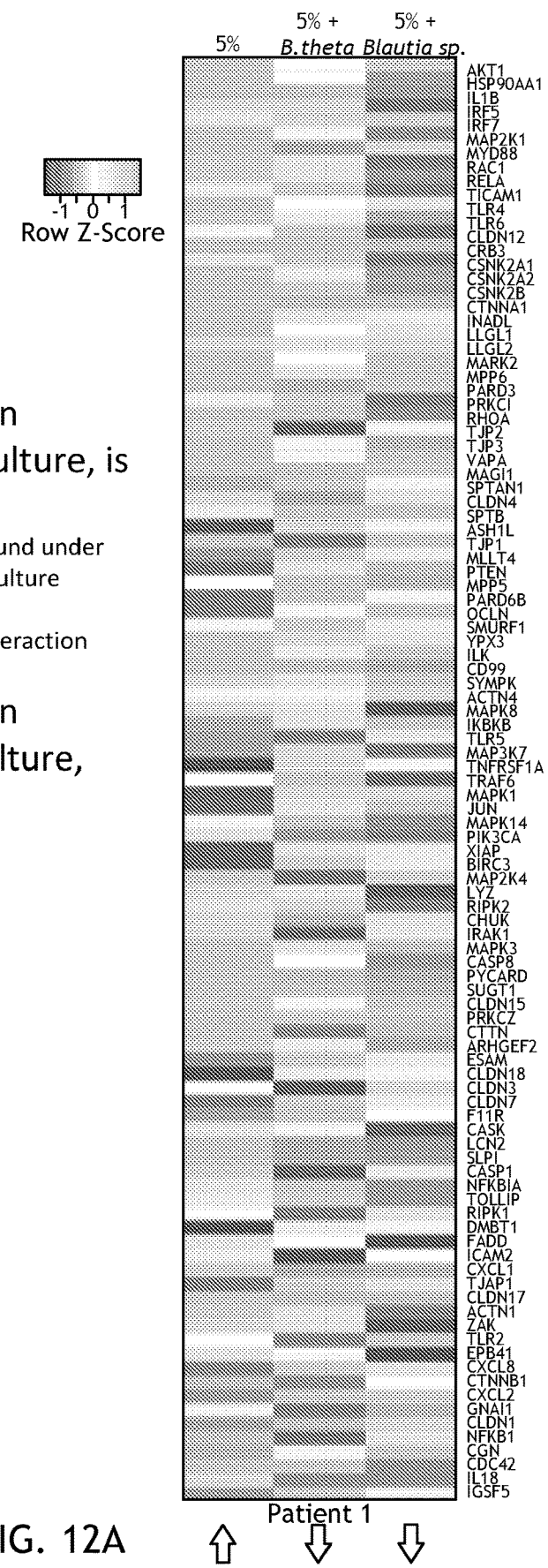
FIG. 12 provides gene expression patterns/profiles in co-culture in response to *B. theta* co-culture.
Figure 12B:
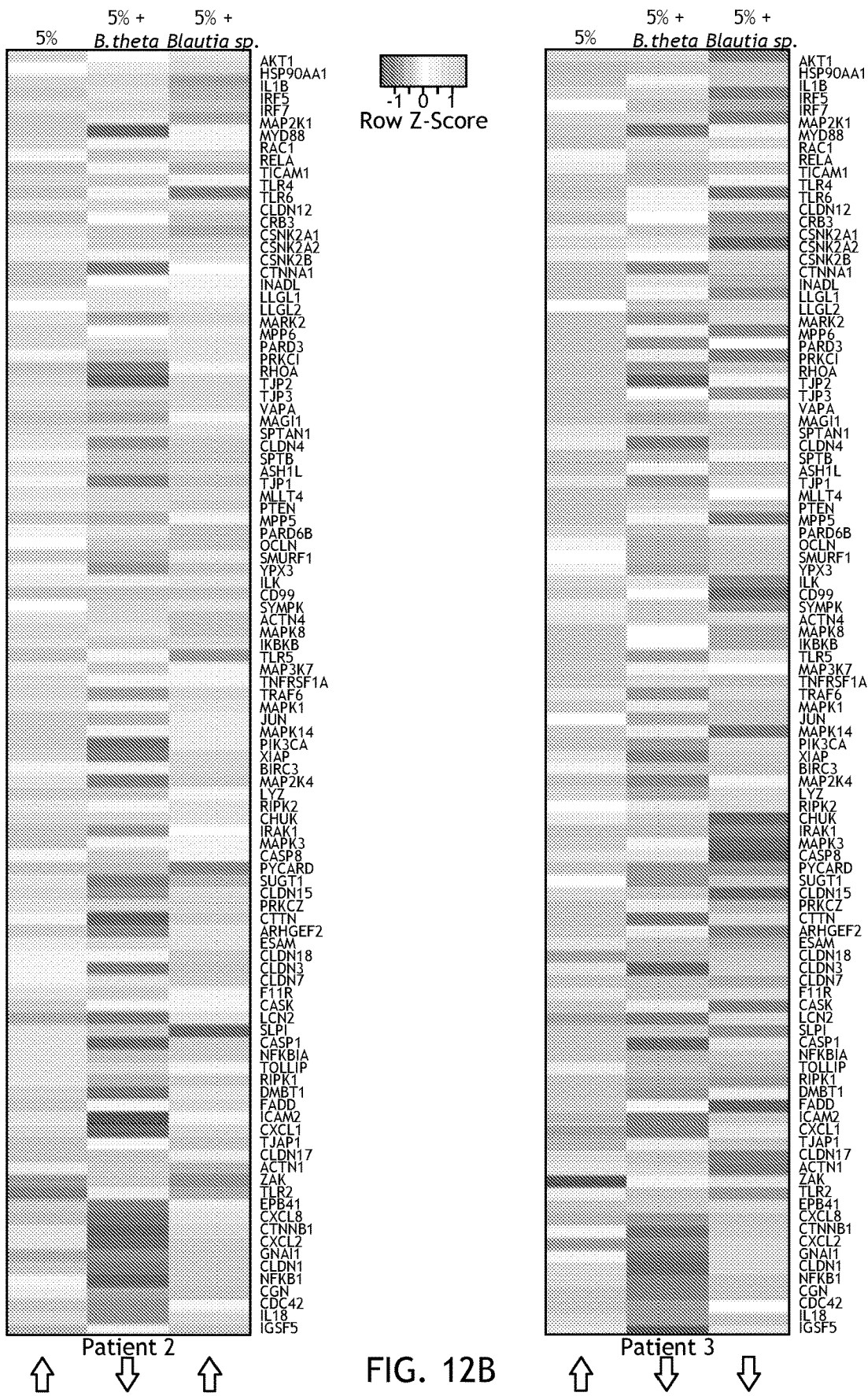

FIG. 12 demonstrates gene expression in co-culture. In FIG. 12, the patient specific response to *Blautia* is further reflected in the epithelial gene expression profile of innate immune and barrier integrity genes. The first column for each of the three panels represents increased expression under hypoxia. All three patient lines reflected a slight reduction in expression when co-culture with *B. thetaiotaomicron*, though many of the genes that significantly changed during hypoxia remained changed following co-culture including, for example, IL-8 expression. However, gene expression in response to *Blautia* co-culture varies between patient lines with Patient 2, as a deviant.

FIG. 13 shows 18 genes that were upregulated during *B. theta* co-culture relative to standard incubator condition, 11 of which were also upregulated during hypoxia. However, the remaining 11 genes were consistently and specifically upregulated in response to *B. theta* co-culture. 13 genes were consistently down-regulated during *B. theta* co-culture hypoxia compared to standard incubator conditions, 3 of which were also downregulated in hypoxia. The remaining 10 genes were consistently and specifically downregulated in response to hypoxia.

Figure 14:
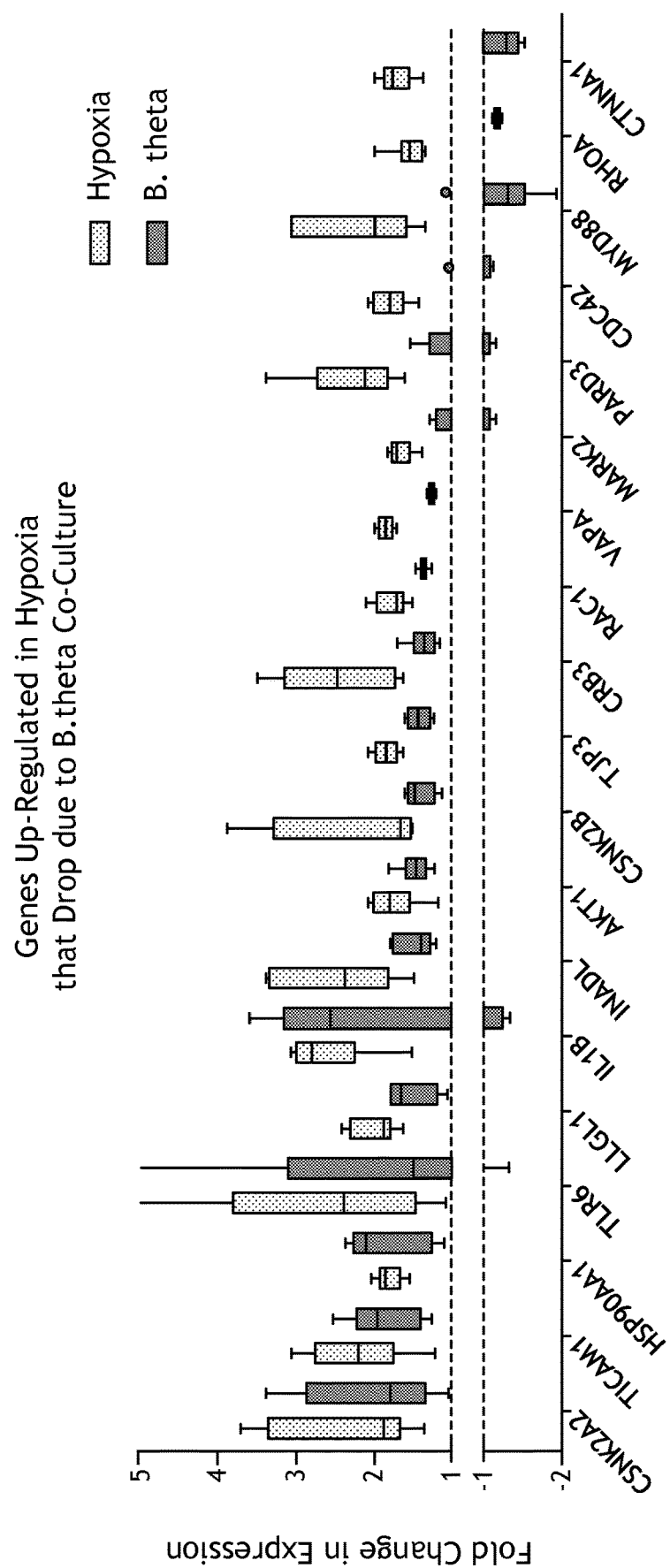
FIG. 14 shows mitigation of genes upregulated during hypoxia following exposure to *B. theta* co culture FIG. 15 demonstrates gene ontology analysis for gene expression in response to 24 hours at 5% oxygen.

FIG. 14 demonstrates that many of the genes consistently upregulated during hypoxia were slightly diminished or mitigated when exposed to *B. theta* co-culture.

Figure 15A:
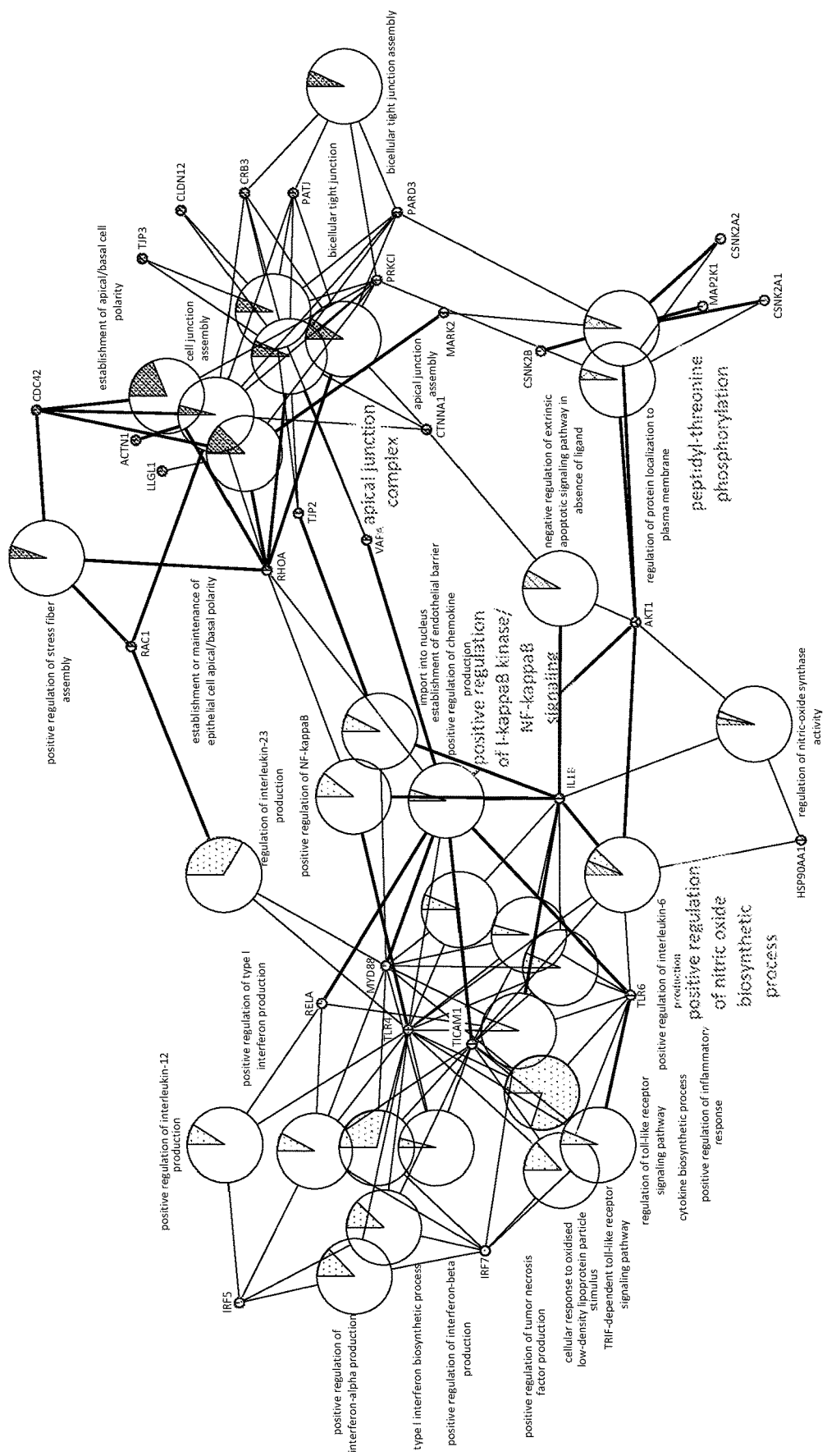

FIG. 15 visualizes (left panel) the top gene ontology pathways induced in response to physiologic hypoxia. The right panel describes the specific pathways activated by physiologic hypoxia.

Figure 16:
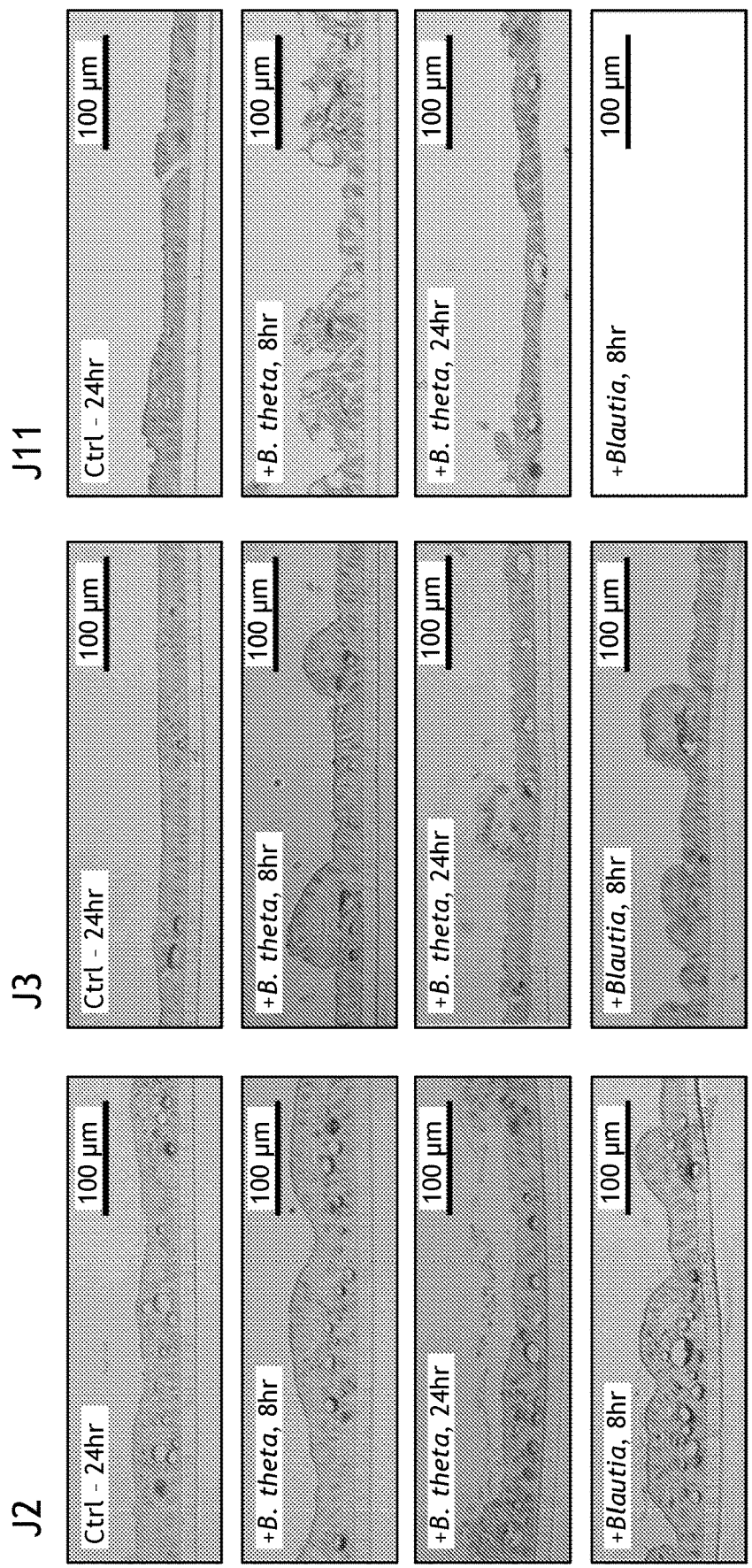
FIG. 16 shows alcian blue stain that suggests that mucin production is dependent on patient lineage.

FIG. 16 depicts histological sections stained with alcian blue (for mucin production) from enteroid monolayers derived from 3 independent patients under conditions of physiologic hypoxia, *B. theta* co-culture, and *Blautia* sp. co-culture. These stains suggest that mucin production, in blue, is dependent more on patient lineage than microbial interaction.

FIG. 17 illustrates the top gene ontology pathways induced in response to *B. theta* co-culture.

Example 3

Exemplary Preparation Method
One embodiment of a method of producing the co-culture system of the disclosure is provided below.
Preparation (Day Before)
  Autoclave the gaskets, lid (if using custom lid), and test tubes caps (or other holder) using liquid 15 setting.
  Allow all elements to cool before proceeding. Using warm gaskets can affect the adhesive seal between gasket and plate during set-up.
  Place 5-10 mL of 1:1 BRM and differentiation media in anaerobic chamber overnight to equilibrate (loosen the cap once in the chamber, this will be your apical media)
Carry Out all Steps Below in a Sterile Tissue Culture Hood
Setting Up the Console
  Place the magnetic stirrer in the inside base of the console
  Open the gas permeable tissue culture plate.
    Avoid touching/indenting the gas permeable membrane on the base of the plate
  Using a 10 ml syringe filled with vacuum grease and with 200 ul pipette tip attached to aid accurate placement, apply vacuum grease to the bottom skirting of the gas permeable tissue culture plate to ensure an air-tight seal and prevent leaks
  Place the gas permeable tissue culture plate base onto the central rubber seal of the console.

Remove the lid from the gas permeable tissue culture plate

Place the lid of the console over the top of the gas permeable tissue culture plate Tighten the console by hand using the screws Stick the plastic binding surface of the silicone/acrylic differential tape on top of the gas permeable tissue culture plate. Do not remove film from top.

Using a blade trim off the excess differential tape from each side of the gas permeable tissue culture plate Taking care to not pierce the lower gas permeable layer of the gas permeable tissue culture plate (i.e. don't put blade too far into the well), use a sterile scalpel carefully carve out the desired wells (every other well) of the gas permeable tissue culture plate Using the edge of the well to guide the blade in a circle to remove tape Use a checkered setup (open every other well) to ensure the gaskets fit Pipette 600 ul of differentiation media into each open well Return the lid of the gas permeable tissue culture plate Preparation of the Gasket/Transwells®

Remove film from top layer of differential tape to expose the rubber binding surface of the adherent tape If necessary, use the electrical tape to wrap around the outside of the plate—this will create a better seal for the lid and prevent the apical media from evaporating.

Set up autoclaved test tubes caps (or other suitable mount) in line to act as mounts for applying the gasket to the Transwell®

Using sterile forceps transfer a gasket to each test tube cap.

Manually remove Transwell® from the 24-well plate and slowly push the Transwell® into the gasket By hand, add each gasket/Transwell® in turn to the gas permeable tissue culture plate Press firmly down to ensure strong binding between differential tape and gasket Add custom lid (see separate methods) to the top of the gas permeable tissue culture plate Standard gas permeable tissue culture plate lid can be used but need to be sealed in place with electrical tape to minimize apical evaporation.

Carry Out all Steps Below in an Anaerobic Hood

Attach the gas tube to the inlet and outlet ports

Carefully remove apical media from Transwell® (this can also be immediately before transferring the setup to the anaerobic chamber)

Add 200-300 ul of the 1:1 BRM/differentiation media (equilibrated from the day before) to the apical side of the monolayer. Replace custom lid.

Place console on magnetic stir plate and *carefully* turn onto a low/medium spin. Doing so too quickly can cause the magnets to shake and knock into the bottom of the gas permeable plate.

Open the blood gas cylinder to turn on the flow from the blood gas into the console Set the gas regulator to the left to flow rate 15 for 30 seconds to purge the chamber Then turn the knob to the right to set the long-term flow rate to 0.5 for the remainder of the experiment.

If running a bacterial co-culture, allow system to equilibrate for 2 hours before adding bacterial to the apical media.

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A co-culture system for co-culturing anaerobic microbes and gut tissue, comprising two or more anaerobic chambers and two or more aerobic chambers, and a gas adjustable chamber comprising a gas;
   wherein each anerobic chamber is removably insertable into a single aerobic chamber;
   wherein each anaerobic chamber comprises a gas permeable base, wherein when a single anaerobic chamber is inserted into the single aerobic chamber, the single anaerobic chamber is gaseously communicable with the single aerobic chamber;
   wherein the gas permeable base comprises gut tissue of a subject in the anaerobic chamber;
   wherein the gut tissues comprises an apical side and a basolateral side; wherein the apical side faces the anaerobic chamber; wherein the apical side is anaerobic and the basolateral side is oxygenated;
   and wherein there is a gas permeable side common to the two or more aerobic chambers and the gas adjustable chamber.

2. The system of claim 1, wherein the system is housed in an anaerobic atmosphere.

3. The system of claim 1, wherein the gas adjustable chamber comprises a mechanism for circulation.

4. The system of claim 1, wherein the gas adjustable chamber is configured to receive the gas via a conduit.

5. The system of claim 4, wherein a source of the gas is a tank.

6. The system of claim 1, wherein the gas is blood gas.

7. The system of claim 6, wherein the blood gas is comprised of oxygen, carbon dioxide, and nitrogen.

8. The system of claim 1, wherein the anaerobic chamber is adapted to be mounted on one or more gaskets.

9. The system of claim 1, wherein the aerobic chamber comprises one or more multi-well plates.

10. The system of claim 1, wherein at least part of the aerobic chamber comprises glass.

11. The system of claim 2, the gas permeable side comprises one or more openings.

12. The system of claim 1, wherein a two-sided adhesive is mounted onto the gas permeable side in the anaerobic chamber.

13. The system of claim 1, wherein the anaerobic chamber is adapted to be mounted onto the aerobic chamber.

14. The system of claim 1, wherein an adapter is mounted onto the aerobic chamber.

15. The system of claim 1, wherein the system comprises a lid.

16. The system of claim 14, wherein the adapter is secured onto the aerobic chamber and the gas adjustable chamber.

17. The system of claim 1, wherein the gut tissue comprises one or more enteroids.

18. The system of claim 1, wherein the gut tissue is plated as a monolayer and differentiated within the anaerobic chamber.

19. The system of claim 1, wherein the anaerobic chamber comprises one or more microbes.

20. The system of claim 19, wherein the one or more microbes are bacteria.

21. The system of claim 20, wherein the one or more bacteria are bacteriodetes, firmicutes, actinobacteria, proteobacteria, verrucomicrobia, or a combination thereof.

22. The system of claim 19, wherein the one or more microbes are viruses.

23. The system of claim 22, wherein the one or more viruses are Rotaviruse, "Norwalk-like" viruse, Adenoviruse, Astroviruse, "Sappro-like" viruse, Toroviruse, Coronaviruse, Picornavirue, and Herpesvirus, or a combination thereof.

24. The system of any one of claim 19, wherein the one or more microbes are fungi.

25. The system of claim 24, wherein the one or more fungi are Ascomycota, Basidiomycota, Mucoromycota, *Saccharomyces, Malassezia, Candida, Cyberlindnera, Penicillium, Cladosporium, Aspergillus, Agaricus, Fusarium, Pichia, Debaryomyces, Galactomyces, Altemaria*, and *Clavispora*, or a combination thereof.

26. The system of claim 1, wherein the anaerobic chamber comprises media for the enteroid cultures.

27. The system of claim 26, wherein the media for the enteroid cultures comprises one or more growth factors in the anaerobic chamber.

\* \* \* \* \*

UNITED STATES PATENT AND TRADEMARK OFFICE
CERTIFICATE OF CORRECTION

PATENT NO. : 12,337,311 B2  
APPLICATION NO. : 16/757577  
DATED : June 24, 2025  
INVENTOR(S) : Tatiana Y. Fofanova et al.

Page 1 of 1

It is certified that error appears in the above-identified patent and that said Letters Patent is hereby corrected as shown below:

In the Claims

Column 20, Claim 11, Line 57, delete reference to "claim 2" and replace with claim 1.

Signed and Sealed this  
Twenty-sixth Day of August, 2025

Coke Morgan Stewart  
*Acting Director of the United States Patent and Trademark Office*